US012708578B2

(12) United States Patent
Kaikenger et al.

(10) Patent No.: US 12,708,578 B2
(45) Date of Patent: Aug. 18, 2026

(54) PATIENT LIFT AND SLING HAVING A SLING LOOP ORIENTATION SENSOR

(71) Applicant: Liko Research & Development AB, Lulea (SE)

(72) Inventors: Philippe Kaikenger, Pluvigner (FR); Clementine Pirio, Vannes (FR); Jean-Bernard Duvert, Auray (FR); Mickael Audic, Locmiquelic (FR); Marcus Linde, Ojebyn (SE); Daniel Johansson, Råneå (SE); Johanna Sundqvist, Gammelstad (SE)

(73) Assignee: Liko Research & Development AB, Lulea (SE)

( * ) Notice: Subject to any disclaimer, the term of this patent is extended or adjusted under 35 U.S.C. 154(b) by 58 days.

(21) Appl. No.: 18/901,086

(22) Filed: Sep. 30, 2024

(65) Prior Publication Data

US 2025/0017797 A1 Jan. 16, 2025

Related U.S. Application Data

(63) Continuation of application No. 18/243,252, filed on Sep. 7, 2023, now Pat. No. 12,121,486, which is a
(Continued)

(51) Int. Cl.
*A61G 7/10* (2006.01)
*A61G 5/14* (2006.01)
(Continued)

(52) U.S. Cl.
CPC ............. *A61G 7/1051* (2013.01); *A61G 7/10* (2013.01); *A61G 7/1001* (2013.01); *G16H 40/63* (2018.01);
(Continued)

(58) Field of Classification Search
CPC ...... A61G 7/1051; A61G 7/10; A61G 7/1001; A61G 5/14; A61G 2203/12;
(Continued)

(56) References Cited

U.S. PATENT DOCUMENTS

| | | | |
|---|---|---|---|
| 1,789,025 | A | 1/1931 | Shepard, Jr. et al. |
| 1,876,832 | A | 9/1932 | Bancroft |

(Continued)

FOREIGN PATENT DOCUMENTS

| | | | |
|---|---|---|---|
| EP | 0241096 | A2 | 10/1987 |
| EP | 1031339 | A2 | 8/2000 |

(Continued)

OTHER PUBLICATIONS

Independent Lifter—The Ideal Patient Lift for Home Care. Oct. 7, 2017, You Tube, https://youtu.be/qHIzn0yRj44?si=kh34V2chXP0C8M0d (Year: 2017).*

(Continued)

*Primary Examiner* — Madison Matthews
(74) *Attorney, Agent, or Firm* — Barnes & Thornburg LLP

(57) ABSTRACT

A person lift system includes a motor and a sling bar coupled to the motor. The sling bar includes a first attachment hook at a first end region of the sling bar and a second attachment hook at a second end region of the sling bar. A sling includes a main body section and a plurality of loops coupled to the main body section. Each of the plurality of loops is configured to attach to one of the plurality of attachment hooks. A first electronic reader is coupled to the sling bar near the first attachment hook. A second electronic reader is coupled to the sling bar near the second attachment hook. Each of a plurality of short range wireless tags is coupled to a respective one of the plurality of loops.

22 Claims, 15 Drawing Sheets

Related U.S. Application Data continuation of application No. 16/750,240, filed on Jan. 23, 2020, now Pat. No. 11,786,430.

(60) Provisional application No. 62/803,686, filed on Feb. 11, 2019.

(51) Int. Cl.
*G16H 10/65* (2018.01)
*G16H 40/63* (2018.01)

(52) U.S. Cl.
CPC ............ *A61G 5/14* (2013.01); *A61G 2203/12* (2013.01); *A61G 2203/30* (2013.01); *A61G 2205/60* (2013.01); *G16H 10/65* (2018.01)

(58) Field of Classification Search
CPC ............ A61G 2203/30; A61G 2205/60; A61G 7/1042; A61G 7/1061; A61G 7/1065; A61G 7/1078; A61G 7/1017; A61G 7/1046; A61G 7/1015; A61G 2203/40; A61G 7/1019; A61G 2200/34; A61G 2200/32; A61G 7/1076; G16H 40/63; G16H 10/65; G16H 40/06; Y10S 414/134
USPC ........... 5/83.1, 86.1, 87.1, 89.1, 81.1 R, 85.1
See application file for complete search history.

(56) References Cited

U.S. PATENT DOCUMENTS

| | | | |
|---|---|---|---|
| 1,878,785 | A | 9/1932 | Leavitt |
| 1,971,294 | A | 8/1934 | Bunker |
| 2,821,406 | A | 1/1958 | Hoyer et al. |
| 2,903,238 | A | 9/1959 | Flandrick |
| 3,013,282 | A | 12/1961 | Volavsek |
| 3,099,842 | A | 8/1963 | Jensen |
| 3,131,404 | A | 5/1964 | Bowers et al. |
| 3,137,011 | A | 6/1964 | Fischer |
| 3,172,551 | A | 3/1965 | Wolfe |
| 3,203,009 | A | 8/1965 | Lundberg |
| 3,222,029 | A | 12/1965 | Hildemann |
| 3,234,568 | A | 2/1966 | Fischer |
| 3,351,959 | A | 11/1967 | Turpin |
| 3,407,413 | A | 10/1968 | James |
| 3,732,584 | A | 5/1973 | James |
| 3,790,974 | A | 2/1974 | Johansson |
| 3,829,916 | A | 8/1974 | James |
| 3,962,737 | A | 6/1976 | James |
| 3,983,584 | A | 10/1976 | Holecek |
| 3,996,632 | A | 12/1976 | Bakker nee Viel |
| 3,998,284 | A | 12/1976 | James |
| 3,999,227 | A | 12/1976 | Ingemansson |
| 4,003,479 | A | 1/1977 | Reyer |
| 4,010,499 | A | 3/1977 | Davis et al. |
| 4,015,725 | A | 4/1977 | Ryan et al. |
| 4,070,721 | A | 1/1978 | Stasko |
| 4,075,719 | A | 2/1978 | Sullivan |
| D247,458 | S | 3/1978 | Johansson |
| 4,091,479 | A | 5/1978 | Hancock |
| 4,095,677 | A | 6/1978 | Johannson |
| 4,117,561 | A | 10/1978 | Zamotin |
| 4,125,908 | A | 11/1978 | Vail et al. |
| 4,138,750 | A | 2/1979 | Michalowski |
| 4,144,713 | A | 3/1979 | Clark et al. |
| 4,206,523 | A | 6/1980 | James |
| 4,232,412 | A | 11/1980 | Petrini |
| 4,255,823 | A | 3/1981 | Boyer et al. |
| 4,278,387 | A | 7/1981 | Seguela et al. |
| 4,296,509 | A | 10/1981 | Simmons et al. |
| 4,372,452 | A | 2/1983 | McCord |
| 4,399,570 | A | 8/1983 | Tracy et al. |
| 4,399,572 | A | 8/1983 | Johansson |
| 4,484,366 | A | 11/1984 | Koontz |
| 4,487,019 | A | 12/1984 | Johansson |
| 4,571,758 | A | 2/1986 | Samuelsson |
| 4,588,155 | A | 5/1986 | James |
| 4,592,695 | A | 6/1986 | McConnell |
| 4,627,119 | A | 12/1986 | Hachey et al. |
| 4,633,538 | A | 1/1987 | James |
| 4,639,955 | A | 2/1987 | Carminati et al. |
| 4,712,257 | A | 12/1987 | James |
| 4,719,655 | A | 1/1988 | Dean |
| 4,739,526 | A | 4/1988 | Hollick |
| 4,742,588 | A | 5/1988 | James |
| 4,882,798 | A | 11/1989 | Worsnop |
| 4,903,355 | A | 2/1990 | Hickerson |
| 4,920,590 | A | 5/1990 | Weiner |
| 4,944,056 | A | 7/1990 | Schroeder et al. |
| 4,944,057 | A | 7/1990 | Shaw |
| 4,947,497 | A | 8/1990 | Marchand |
| 4,969,221 | A | 11/1990 | Foster |
| 4,999,862 | A | 3/1991 | Hefty |
| 5,018,933 | A | 5/1991 | Kramer |
| 5,022,106 | A | 6/1991 | Richards |
| 5,072,840 | A | 12/1991 | Asakawa et al. |
| 5,103,509 | A | 4/1992 | Richards |
| D327,763 | S | 7/1992 | Silbersky et al. |
| 5,309,584 | A | 5/1994 | Parker |
| 5,333,333 | A | 8/1994 | Mah |
| 5,337,908 | A | 8/1994 | Beck, Jr. |
| 5,348,273 | A | 9/1994 | Sandell et al. |
| 5,355,538 | A | 10/1994 | Fulford et al. |
| 5,369,821 | A | 12/1994 | Richards et al. |
| D355,293 | S | 2/1995 | Parker |
| 5,396,670 | A | 3/1995 | Firebaugh et al. |
| 5,442,821 | A | 8/1995 | Weeks |
| 5,615,426 | A | 4/1997 | Hokett |
| 5,682,630 | A | 11/1997 | Simon |
| 5,685,033 | A | 11/1997 | Lavin |
| 5,692,253 | A | 12/1997 | Keijser et al. |
| 5,694,654 | A | 12/1997 | Roy |
| 5,697,109 | A | 12/1997 | Hodgetts |
| 5,697,110 | A | 12/1997 | Campbell |
| 5,708,993 | A | 1/1998 | Campbell et al. |
| 5,711,044 | A | 1/1998 | Newman et al. |
| 5,729,843 | A | 3/1998 | Manthey |
| 5,758,371 | A | 6/1998 | VanDyke et al. |
| 5,784,729 | A | 7/1998 | Dunn et al. |
| 5,802,633 | A | 9/1998 | Capaldi |
| 5,809,591 | A | 9/1998 | Capaldi et al. |
| 5,810,104 | A | 9/1998 | Campbell |
| 5,819,338 | A | 10/1998 | Hession |
| 5,853,015 | A | 12/1998 | Evans |
| 5,987,664 | A | 11/1999 | Somerton et al. |
| 6,039,376 | A | 3/2000 | Lopreiato |
| 6,073,280 | A | 6/2000 | Farnum |
| 6,092,247 | A | 7/2000 | Wilson |
| 6,122,778 | A | 9/2000 | Cohen |
| 6,161,233 | A | 12/2000 | Von Schroeter et al. |
| 6,175,973 | B1 | 1/2001 | Hakamiun et al. |
| 6,219,862 | B1 | 4/2001 | Horcher et al. |
| 6,289,534 | B1 | 9/2001 | Hakamiun et al. |
| 8,474,794 | B2 | 7/2013 | Liljedahl |
| 8,856,981 | B1 * | 10/2014 | Rayess ................. A61G 7/1067 5/89.1 |
| 8,978,905 | B2 | 3/2015 | Bergenstraale et al. |
| 9,408,765 | B2 | 8/2016 | Andersson et al. |
| 9,463,128 | B2 | 10/2016 | Ng |
| 9,527,699 | B2 | 12/2016 | Liljedahl |
| 9,693,922 | B2 | 7/2017 | Andersson et al. |
| 9,711,029 | B2 * | 7/2017 | Ribble .................. A61B 5/1115 |
| 9,796,168 | B2 | 10/2017 | Bergenstråle et al. |
| 9,875,582 | B2 | 1/2018 | Bolin et al. |
| 10,045,895 | B2 | 8/2018 | Eklof et al. |
| 10,138,102 | B2 | 11/2018 | Baillargeon et al. |
| 10,251,796 | B2 | 4/2019 | Eriksson et al. |
| 10,322,046 | B2 | 6/2019 | Liljedahl |
| 10,376,434 | B2 | 8/2019 | Andersson et al. |
| 10,420,690 | B2 | 9/2019 | Dixon et al. |
| 10,478,360 | B2 | 11/2019 | Andersson et al. |
| 10,478,361 | B2 | 11/2019 | Harmeyer et al. |
| 10,561,558 | B2 | 2/2020 | Kaikenger |
| 10,596,052 | B2 | 3/2020 | Andersson et al. |
| 10,610,431 | B2 | 4/2020 | Andersson et al. |

(56) References Cited

U.S. PATENT DOCUMENTS

| | | | | |
|---|---|---|---|---|
| 11,786,430 | B2 | 10/2023 | Kaikenger et al. | |
| 12,121,486 | B2 | 10/2024 | Kaikenger et al. | |
| 2010/0097181 | A1 * | 4/2010 | Sorensen | A61G 7/1065 294/74 |
| 2012/0000876 | A1 | 1/2012 | Bergenstraale et al. | |
| 2013/0091631 | A1 | 4/2013 | Hayes et al. | |
| 2013/0116604 | A1 | 5/2013 | Morilla et al. | |
| 2014/0020175 | A1 * | 1/2014 | Dixon | G16H 40/63 5/85.1 |
| 2014/0115778 | A1 | 5/2014 | Ng | |
| 2015/0136313 | A1 | 5/2015 | Bergenstråle et al. | |
| 2017/0000672 | A1 | 1/2017 | Andersson et al. | |
| 2017/0027794 | A1 * | 2/2017 | Andersson | A61G 7/1017 |
| 2017/0325524 | A1 | 11/2017 | Hyde et al. | |
| 2017/0325525 | A1 * | 11/2017 | Hyde | A61G 7/1051 |
| 2017/0326013 | A1 * | 11/2017 | Hyde | A61G 7/108 |
| 2020/0253801 | A1 | 8/2020 | Kaikenger et al. | |
| 2023/0414428 | A1 | 12/2023 | Kaikenger et al. | |

FOREIGN PATENT DOCUMENTS

| | | | |
|---|---|---|---|
| EP | 1647250 | A1 | 4/2006 |
| EP | 2604241 | A1 | 6/2013 |
| EP | 2684549 | A2 | 1/2014 |
| EP | 2777675 | A1 | 9/2014 |
| EP | 2862552 | A1 | 4/2015 |
| EP | 3111907 | A1 | 1/2017 |
| EP | 3123998 | A1 | 2/2017 |
| FR | 2414909 | A1 | 8/1979 |
| FR | 2461492 | A1 | 2/1981 |
| GB | 867149 | A | 5/1961 |
| WO | 1990001916 | A1 | 3/1990 |
| WO | 1997017048 | A1 | 5/1997 |
| WO | 1997030675 | A1 | 8/1997 |
| WO | 2008007222 | A2 | 1/2008 |
| WO | 2008029272 | A2 | 3/2008 |
| WO | 2013034936 | A1 | 3/2013 |

OTHER PUBLICATIONS

"Independent Lifter■—The Ideal Patient Lift for Home Care." Oct. 7, 2017, YouTube, www.youtube.com/watch?vqHizn0yRj44 (Year: 2017).

* cited by examiner

PATIENT LIFT AND SLING HAVING A SLING LOOP ORIENTATION SENSOR

CROSS-REFERENCE TO RELATED APPLICATIONS

This application is a continuation of U.S. application Ser. No. 18/243,252, filed Sep. 7, 2023, now U.S. Pat. No. 12,121,486, which is a continuation of U.S. application Ser. No. 16/750,240, filed Jan. 23, 2020, now U.S. Pat. No. 11,786,430, which claims the benefit under 35 U.S.C. § 119(e) of U.S. Provisional Patent Application No. 62/803,686, filed Feb. 11, 2019, each of which is hereby expressly incorporated by reference herein in its entirety.

BACKGROUND

The present disclosure relates to patient lift systems and particularly, to patient lift systems having a sling attached to a sling bar that is raised and lowered by a motor. More particularly, the present disclosure relates to systems and methods for enabling the motors of patient lift systems for operation.

Patient lift systems generally include a motor coupled to a sling bar to raise and lower the sling bar. A sling is attached to the sling bar and is configured to support and suspend a patient from the sling bar. The patient is raised and lowered in the sling by activating the motor. Such patient lift systems are sometimes used to move patients onto and off of patient support apparatuses. To attach the sling to the sling bar, loops of the sling are coupled to attachment hooks of the sling bar. A common type of sling has four loops, two of which are coupled to each hook of the sling bar. Failure to properly attach the correct pair of loops to the corresponding attachment hook may increase the risk of a patient fall. Thus, a patient lift system in which caregivers are assured of proper connection of the loops of slings to hooks of respective sling bars would be welcomed in the art.

Additionally, caregivers have a need for keeping track of the number of performed lifts in each sling. Also, healthcare facilities have a need to track laundering and usage of the sling so that the sling may be replaced prior to an accident caused by a worn sling. Moreover, caregivers require ease of access when using the patient lift system. In some prior art patient lift systems, the controls of the patient lift system prevent the caregiver from maintaining two hands on the patient when lifting and lowering the patient.

SUMMARY

The present disclosure includes one or more of the features recited in the appended claims and/or the following features which, alone or in any combination, may comprise patentable subject matter.

According to one aspect of the disclosed embodiments, a person lift system may have a motor and a sling bar coupled to the motor. The sling bar may have a first attachment hook at a first end region of the sling bar and a second attachment hook at a second end region of the sling bar. A sling may have a main body section and a plurality of loops coupled to the main body section. Each of the plurality of loops may be configured to attach to one of the plurality of attachment hooks. A first electronic reader may be coupled to the sling bar near the first attachment hook. A second electronic reader may be coupled to the sling bar near the second attachment hook. Each of a plurality of short range wireless tags may be coupled to a respective one of the plurality of loops. The first and second electronic readers may read short range tag identification signals from the short range wireless tags to determine whether a proper first subset of the plurality of loops is coupled to the first attachment hook and a proper second subset of the plurality of loops is coupled to the second attachment hook.

In some embodiments, a patient tag may be coupled to a patient. Operation of the motor may be enabled in response to the first electronic reader or the second electronic reader reading the patient tag. A caregiver tag may be coupled to a caregiver. Operation of the motor may be enabled in response to the first electronic reader or the second electronic reader reading the caregiver tag. Operation of the motor may be enabled in response to the first electronic reader and the second electronic reader confirming that the first subset of the plurality of loops is coupled to the first attachment hook and the second subset of the plurality of loops is coupled to the second attachment hook. Operation of the motor may be enabled in response to at least one of (i) the first electronic reader or the second electronic reader reading the patient tag, (ii) the first electronic reader or the second electronic reader reading the caregiver tag, or (iii) the first electronic reader confirming that the first subset of the plurality of loops is coupled to the first attachment hook and the second electronic reader confirming that the second subset of the plurality of loops is coupled to the second attachment hook. Alternatively, operation of the motor may be enabled in response to all of (i) the first electronic reader or the second electronic reader reading the patient tag, (ii) the first electronic reader or the second electronic reader reading the caregiver tag, and (iii) the first electronic reader confirming that the first subset of the plurality of loops is coupled to the first attachment hook and the second electronic reader confirming that the second subset of the plurality of loops is coupled to the second attachment hook.

Optionally, each of a plurality of accelerometers may be coupled to a respective loop of the plurality of loops. Each accelerometer may be configured to determine an orientation of the respective loop with respect to a direction of gravity or with respect to horizontal. Each accelerometer may determine movement of the sling so that a processor coupled to the accelerometer may be able to determine whether the sling is in a laundry cycle.

It may be desired that a control system controls the motor. The control system may be enabled in response to the first electronic reader or the second electronic reader reading one of the plurality of short range wireless tags. The control system may track a number of person lift system uses based on the first electronic reader or the second electronic reader reading one of the plurality of short range wireless tags.

Alternatively or additionally, a user input may be configured to operate the motor. The user input may be coupled to the sling. The user input may be detachably coupled to the sling. A retractable tether may couple the user input to the sling bar. It is contemplated by this disclosure that each of the plurality of short range wireless tags may include a radio frequency identification tag.

In some embodiments, each of the first attachment hook and the second attachment hook may be moveable between and an open position and a closed position. Each of the first attachment hook and the second attachment hook may have a sensor to determine whether the respective attachment hook is in the open position or closed position. The first electronic reader may become powered in response to the respective sensor indicating that the first attachment hook may have been moved to the open position. The second electronic reader may become powered in response to the respective sensor indicating that the second attachment hook may have been moved to the open position.

Optionally, a switch may be positioned in the sling. A spring may be coupled to the switch. The spring may activate the switch in response to weight being applied to the sling. In response to the switch being activated, power may be supplied to the plurality of short range wireless tags. It is contemplated by this disclosure that a humidity sensor may be positioned in the sling to detect that the sling is being laundered.

Alternatively or additionally, a wireless communication device may be positioned in the sling to communicate to a remote device that the sling is in use. The remote device may be operable to determine a location of the sling.

Optionally, the sling may have a leg section that may be coupled to the main body section. The leg section may have pressure sensors to detect a pressure on a patient in the sling. The main body section may not include pressure sensors.

According to another aspect of the disclosed embodiments, a person lift system may have a motor and a sling bar coupled to the motor. The sling bar may have a plurality of attachment hook. A sling may have a main body section and a plurality of loops extending from the main body section. Each of the plurality of loops may be configured to attach to one of the plurality of attachment hooks. A handheld controller may have a clip configured to attach to one of the plurality of loops. The handheld controller may have user inputs that are configured to control the motor.

Optionally, the user inputs may have a first button and a second button. One of the first and second buttons may be usable to actuate the motor to raise the sling bar and the other of the first and second buttons may be usable to actuate the motor to lower the sling bar. The handheld controller may have an accelerometer to determine an orientation of the handheld controller. A signal from the accelerometer may be used by a processor to determine an upper button of the first and second buttons and a lower button of the first and second buttons. The upper button may be configured to actuate the motor to raise the sling bar. The lower button may be configured to actuate the motor to lower the sling bar. A retractable cord may couple the handheld controller to the sling bar.

According to yet another aspect of the disclosed embodiments, a person lift system may include a motor and a sling bar coupled to the motor. The sling bar may have a plurality of attachment hooks. A sling may have a main body section and a plurality of loops extending from the main body section. Each of the plurality of loops may be configured to attach to one of the plurality of attachment hooks. A handle may be coupled to one of the plurality of loops. The handle may have a detector in communication with the motor. The handle may be operable to be pulled upwardly and downwardly. In response to the detector detecting an upward force on the handle, the motor may be actuated to raise the sling bar. In response to the detector detecting a downward force on the handle, the motor may be actuated to lower the sling bar.

It is contemplated by the present disclosure that a wireless communication device may be positioned in the sling to communicate to a remote device that the sling is in use. The remote device may track a number of sling uses.

In some embodiments, the detector may include at least one strain gauge. The at least one strain gauge may have a first strain gauge to detect upward movement of the handle and a second strain gauge to detect downward movement of the handle. Optionally, the detector may include an accelerometer.

If desired, the handle may be movably attached to the one of the plurality of loops. For example, the handle may be configured to slide along a length of the one of the plurality of loops.

According to a further aspect of the disclosed embodiments, a person lift system may have a motor and a sling bar coupled to the motor. The sling bar may have a plurality of attachment hooks. A sling may have a main body section and a plurality of loops extending from the main body section. Each of the plurality of loops may be configured to attach to one of the plurality of attachment hooks. A strain gauge may be positioned in one of the plurality of loops. The strain gauge may detect force on the one of the plurality of loops to determine that the sling is in use.

In some embodiments, a wireless communication device may be positioned in the sling to communicate a number of sling uses to a remote computer. Optionally, the strain gauge may be a thread woven into a fabric of the sling.

It is contemplated by the present disclosure that the motor may be enabled in response to the strain gauge detecting force on one of the plurality of loops. A switch may enable the motor in response to the strain gauge detecting the force on one of the plurality of loops. The switch may enable the motor in response to the strain gauge detecting a predetermined weight on one of the plurality of loops.

If desired, pressures sensors may be positioned in a leg section of the sling. The switch may enable the motor in response to the strain gauge detecting the force on one of the plurality of loops and the pressure sensors detecting pressure in the leg section.

According to yet a further aspect of the disclosed embodiments, a person lift system may have a motor and a sling bar coupled to the motor. The sling bar may have an attachment hook. A sling may have a main body section and a loop coupled to the main body section. The loop may be configured to attach to the attachment hook. An electronic reader may be coupled to the sling bar near the attachment hook. A short range wireless tag may be coupled to the loop. The electronic reader may read short range tag identification signals from the short range wireless tag to determine whether the loop is coupled to the attachment hook. A patient tag may be coupled to a patient. A caregiver tag may be coupled to a caregiver. Operation of the motor may be enabled in response to at least one of (i) the electronic reader reading the patient tag, (ii) the electronic reader reading the caregiver tag, or (iii) the electronic reader confirming that the loop is coupled to the attachment hook.

Optionally, the motor may be enabled in response to all of (i) the electronic reader reading the patient tag, (ii) the electronic reader reading the caregiver tag, and (iii) the electronic reader confirming that the loop is coupled to the attachment hook.

Alternatively or additionally, an accelerometer may be coupled to the loop and configured to determine an orientation of the loop with respect to a direction of gravity or with respect to horizontal. The accelerometer may determine movement of the sling so that a processor coupled to the accelerometer is able to determine whether the sling is in a laundry cycle.

It may be contemplated that a control system controls the motor. The control system may be enabled in response to the electronic reader reading the short range wireless tag. The control system may track a number of person lift system uses based on the electronic reader reading the short range wireless tag.

In some embodiments, a user input may be configured to operate the motor. The user input may be coupled to the sling. The user input may be detachably coupled to the sling. A retractable tether may couple the user input to the sling bar. Optionally, the short range wireless tag may include a radio frequency identification tag.

In some embodiments, the attachment hook may be moveable between and an open position and a closed position. The attachment hook may have a sensor to determine whether the attachment hook is in the open position or closed position. The electronic reader may be powered in response to the sensor indicating that the attachment hook may have been moved to the open position.

If desired, a switch may be positioned in the sling. A spring may be coupled to the switch. The spring may activate the switch in response to weight being applied to the sling. In response to the switch being activated, power may be supplied to the short range wireless tag.

Alternatively or additionally, a humidity sensor may be positioned in the sling to detect that the sling is being laundered. Optionally, a wireless communication device may be positioned in the sling to communicate to a remote device that the sling is in use. The remote device may be operable to determine a location of the sling.

It is contemplated by this disclosure that a leg section may be coupled to the main body section. The leg section may have pressure sensors to detect a pressure on a patient in the sling. The main body section may not include pressure sensors.

In some embodiments, a handheld controller may have a clip configured to attach to the loop. The handheld controller may have user inputs that are configured to control the motor. The user inputs may have a first button and a second button. One of the first button and the second button may be usable to actuate the motor to raise the sling bar and the other of the first button and the second button may be usable to actuate the motor to lower the sling bar. The handheld controller may have an accelerometer to determine an orientation of the handheld controller. A signal from the accelerometer may be used by a processor to determine an upper button of the first button and the second button and a lower button of the first button and the second button. The upper button may be configured to actuate the motor to raise the sling bar. The lower button may be configured to actuate the motor to lower the sling bar. A retractable cord may couple the handheld controller to the sling bar.

According to one aspect of the disclosed embodiments, a person lift system may include a motor and a sling bar coupled to the motor. The sling bar may have an attachment hook. A sling may have a main body section and a loop coupled to the main body section. The loop may be configured to attach to the attachment hook. An electronic reader may be coupled to the sling bar near the attachment hook. A short range wireless tag may be coupled to the loop. The electronic reader may read short range tag identification signals from the short range wireless tag to determine whether the loop is coupled to the attachment hook. An accelerometer may be coupled to the loop and configured to determine an orientation of the loop with respect to a direction of gravity or with respect to horizontal.

In some embodiments, the accelerometer may determine movement of the sling so that a processor is able to determine whether the sling is in a laundry cycle. Optionally, a control system may control the motor. The control system may be enabled in response to the electronic reader reading the short range wireless tag. The control system may track a number of person lift system uses based on the electronic reader reading the short range wireless tag.

Alternatively or additionally, a user input may be configured to operate the motor. The user input may be coupled to the sling. The user input may be detachably coupled to the sling. A retractable tether may couple the user input to the sling bar. If desired, the short range wireless tag may include a radio frequency identification tag.

It is contemplated by the present disclosure that the attachment hook may be moveable between and an open position and a closed position. The attachment hook may have a sensor to determine whether the attachment hook is in the open position or closed position. The electronic reader may be powered in response to the sensor indicating that the attachment hook may have been moved to the open position.

Optionally, a switch may be positioned in the sling. A spring may be coupled to the switch. The spring may enable the switch in response to weight being applied to the sling. In response to the switch being activated, power may be supplied to the short range wireless tag.

In some embodiments, a humidity sensor may be positioned in the sling to detect that the sling is being laundered. If desired, a wireless communication device may be positioned in the sling to communicate to a remote device that the sling is in use. The remote device may be operable to determine a location of the sling.

Alternatively or additionally, the sling may have a leg section coupled to the main body section. The leg section may have pressure sensors to detect a pressure on a patient in the sling. The main body section may not include pressure sensors.

Optionally, a handheld controller may have a clip configured to attach to the loop. The handheld controller may have user inputs that are configured to control the motor. The user inputs may have a first button and a second button. One of the first button and the second button may be usable to actuate the motor to raise the sling bar and the other of the first button and the second button may be usable to actuate the motor to lower the sling bar. The handheld controller may have an accelerometer to determine an orientation of the handheld controller. A signal from the accelerometer may be used by a processor to determine an upper button of the first button and the second button and a lower button of the first button and the second button. The upper button may be configured to actuate the motor to raise the sling bar. The lower button may be configured to actuate the motor to lower the sling bar. A retractable cord may couple the handheld controller to the sling bar.

According to another aspect of the disclosed embodiments, a method of operating a person lift system may include coupling a first loop of a sling to a first attachment hook of a sling bar. The sling bar may have a first electronic reader near the first attachment hook. The first loop may have a first short range wireless tag. The method may also include coupling a second loop of the sling to a second attachment hook of the sling bar. The sling bar may have a second electronic reader near the second attachment hook. The second loop may have a second short range wireless tag. The method may further include reading short range tag identification signals from the first short range wireless tag to determine whether the first loop is coupled to the first attachment hook. The method may also include reading short range tag identification signals from the second short range wireless tag to determine whether the second loop is coupled to the second attachment hook.

In some embodiments, the method includes enabling operation of a motor in response to the first electronic reader or the second electronic reader reading a patient tag. The method may also include enabling operation of a motor in response to the first electronic reader or the second electronic reader reading a caregiver tag. The method may further include enabling operation of a motor in response to the first electronic reader confirming that the first loop is coupled to the first attachment hook and the second electronic reader confirming that the second loop is coupled to the second attachment hook. The method may include enabling operation of a motor in response to at least one of (i) the first electronic reader or the second electronic reader reading a patient tag, (ii) the first electronic reader or the second electronic reader reading a caregiver tag, or (iii) the first electronic reader confirming that the first loop is coupled to the first attachment hook and the second electronic reader confirming that the second loop is coupled to the second attachment hook. Alternatively, the method may include enabling operation of a motor in response to all of (i) the first electronic reader or the second electronic reader reading a patient tag, (ii) the first electronic reader or the second electronic reader reading a caregiver tag, and (iii) the first electronic reader confirming that the first loop is coupled to the first attachment hook and the second electronic reader confirming that the second loop is coupled to the second attachment hook.

Optionally, the method may also include determining an orientation of the respective loop with respect to a direction of gravity or with respect to horizontal using an accelerometer coupled to the loop. The method may also include determining movement of the sling with the accelerometer to determine whether the sling is in a laundry cycle.

Alternatively or additionally, the method may include enabling a control system coupled to the motor in response to the first electronic reader reading the first short range wireless tag or the second electronic reader reading the second short range wireless tag. The method may also include tracking a number of person lift system uses with the control system based on the first electronic reader or the second electronic reader reading one of the respective first or second short range wireless tag.

It is contemplated by the present disclosure that the method may further include operating the motor with a user input. The user input may be coupled to the sling. The user input may be detachably coupled to the sling. The method may also include coupling the user input to the sling bar with a retractable tether. In some embodiments, each of the first and second short range wireless tags includes a radio frequency identification tag.

If desired, each of the first attachment hook and the second attachment hook may be moveable between and an open position and a closed position. The method may also include determining whether the respective attachment hook is in the open position or closed position with a sensor. The method may also include powering the first electronic reader in response to the sensor of the first attachment hook being moved to the open position. The method may also include powering the second electronic reader in response to the sensor of the second attachment hook being moved to the open position.

In some embodiments, the method may also include activating a switch positioned in the sling in response to weight being applied to the sling to supply power to the first and second short range wireless tags. Optionally, the method may further include detecting that the sling is being laundered using a humidity sensor positioned in the sling.

It is contemplated by this disclosure that the method may include communicating to a remote device that the sling is in use with a wireless communication device positioned in the sling. The method may also include determining a location of the sling with the remote device.

Optionally, the method may also include detecting a pressure on a patient in the sling with a pressure sensor positioned in a leg section of the sling. A main body section of the sling may not include pressure sensors.

According to another aspect of the disclosed embodiments, a method of operating a person lift system may include coupling a loop of a sling to an attachment hook of a sling bar. The sling bar may have an electronic reader near the attachment hook. The loop may have a short range wireless tag. The method may also include reading a short range tag identification signal from the short range wireless tag to determine whether the loop is coupled to the attachment hook. The method may also include reading a first identification signal from a patient tag coupled to a patient and reading a second identification signal from a caregiver tag coupled to a caregiver. The method may further include enabling operation of the motor in response to at least one of (i) the electronic reader reading the patient tag, (ii) the electronic reader reading the caregiver tag, or (iii) the electronic reader confirming that the loop is coupled to the attachment hook. Optionally, the method may also include enabling operation of the motor in response to all of (i) the electronic reader reading the patient tag, (ii) the electronic reader reading the caregiver tag, and (iii) the electronic reader confirming that the loop is coupled to the attachment hook. If desired, that the method also may include determining an orientation of the loop with respect to a direction of gravity or with respect to horizontal using an accelerometer. The method may also include determining movement of the sling with the accelerometer to determine whether the sling is in a laundry cycle.

Alternatively or additionally, the method may also include activating a control system in response to the electronic reader reading the short range wireless tag. The method may also include tracking a number of person lift system uses with the control system based on the electronic reader reading the short range wireless tag.

In some embodiments, the method may also include operating the motor with a user input. The user input may be coupled to the sling. The user input may be detachably coupled to the sling. The method may also include coupling the user input to the sling bar with a retractable tether. In some embodiments, the short range wireless tag may be a radio frequency identification tag.

If desired, the attachment hook may be moveable between and an open position and a closed position. The method may also include determining whether the attachment hook is in the open position or closed position with a sensor. The method may further include powering the electronic reader in response to the sensor of the attachment hook being moved to the open position.

In some embodiments, the method may also include activating a switch in response to weight being applied to the sling to supply power to the short range wireless tag. Optionally, the method may also include detecting that the sling is being laundered with a humidity sensor positioned in the sling.

Alternatively or additionally, the method may also include communicating to a remote device that the sling is in use with a wireless communication device positioned in the sling. The method may also include determining a location of the sling with the remote device.

If desired, the method may include detecting a pressure on a patient in the sling with a pressure sensor positioned in a leg section of the sling. A main body section of the sling may not include pressure sensors.

In some embodiments, the method also may include controlling the motor with a handheld controller having a clip configured to attach to the loop. The handheld controller may include a first button and a second button. The method may also include actuating the motor to raise the sling bar with one of the first button and the second button. The method may further include actuating the motor to lower the sling bar with the other of the first button and the second button. The handheld controller may have an accelerometer to determine an orientation of the handheld controller. The method may also include determining an upper button of the first button and the second button with the accelerometer and determining a lower button of the first button and the second button with the accelerometer. The method may also include actuating the motor with the upper button to raise the sling bar. The method may also require actuating the motor with the lower button to lower the sling bar.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

Figure 4:
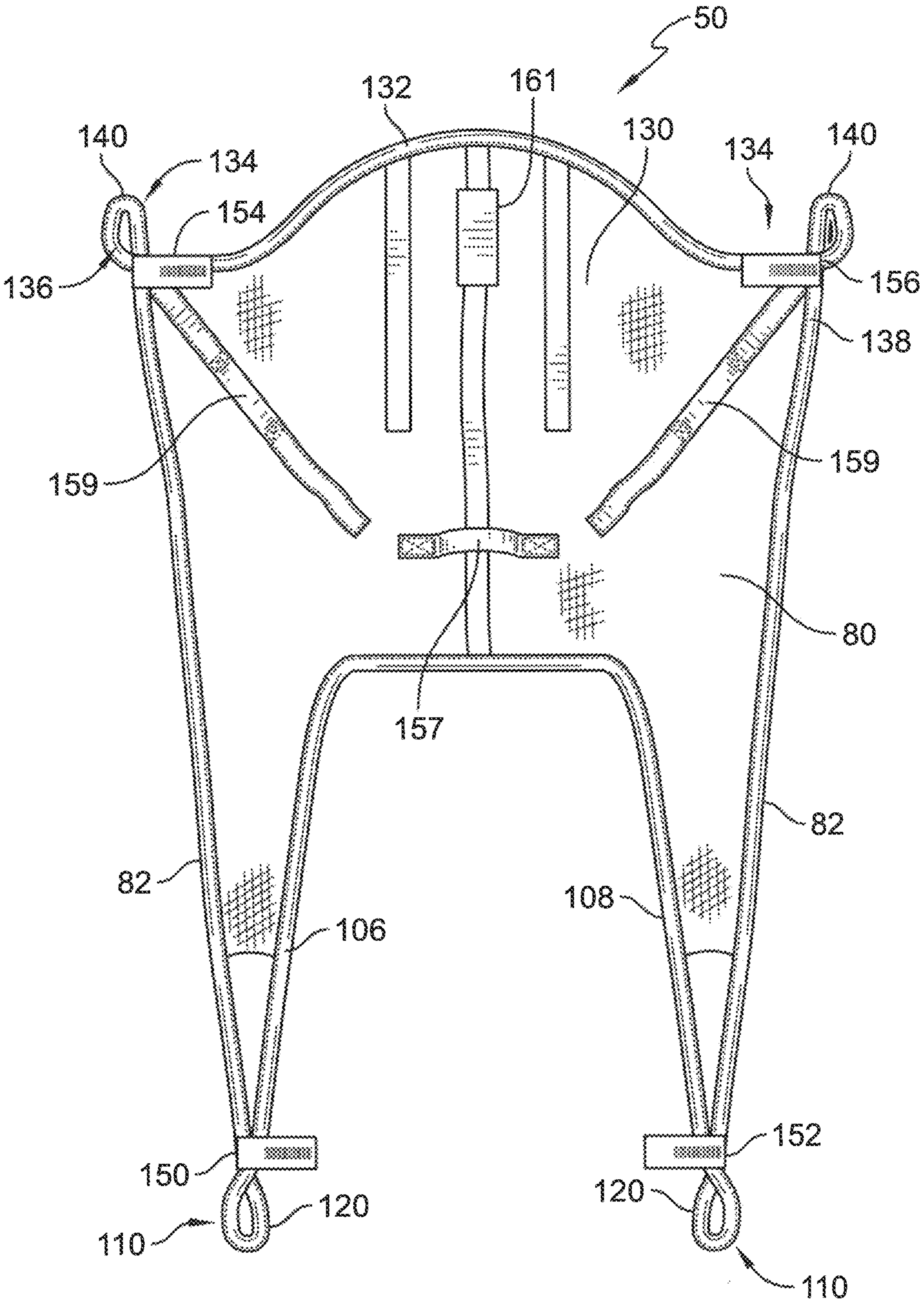
FIG. 4 is a top plan view of the sling of FIG. 3 showing the sling having a body section, a first pair of loops at opposite upper corner regions of the body section, a pair of leg sections extending downwardly from the body section, and a second pair of loops at lower ends of the leg sections.
Figure 15:
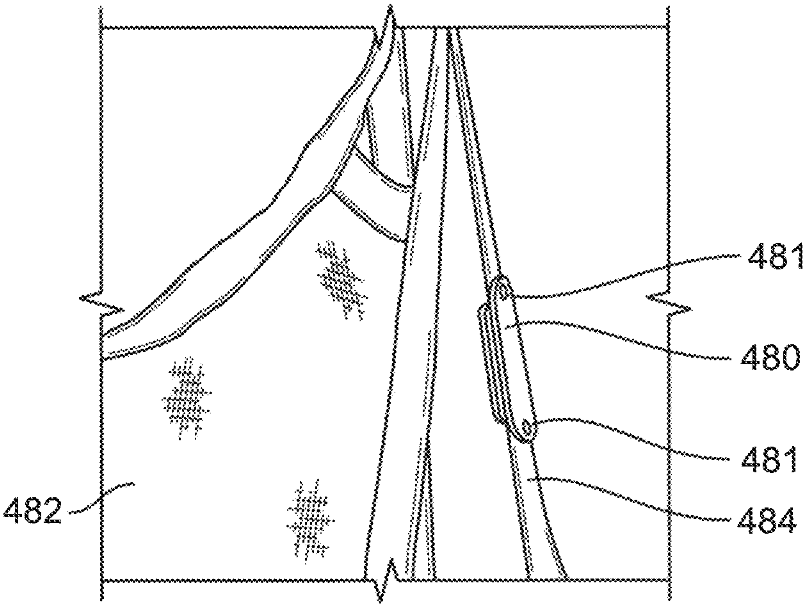
FIG. 15 is a front perspective view of a sling in accordance with yet another embodiment of the present disclosure showing a lift system controller removably clipped to a strap of the sling.
Figure 17:
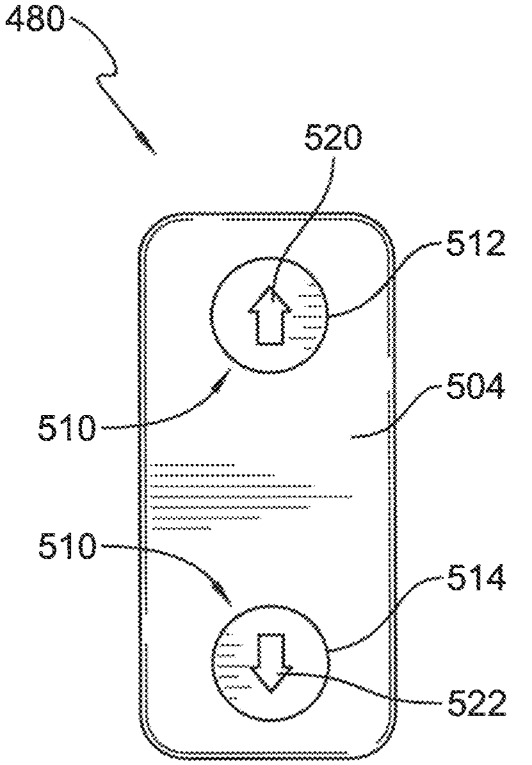
Figure 19:
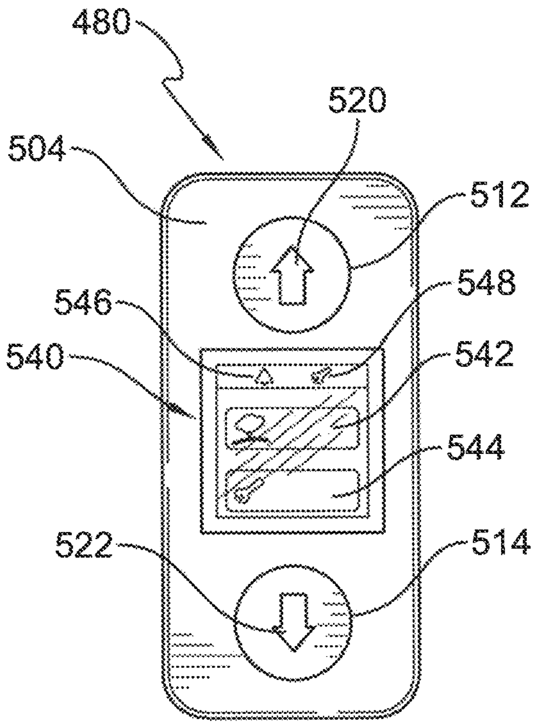
Figure 18:
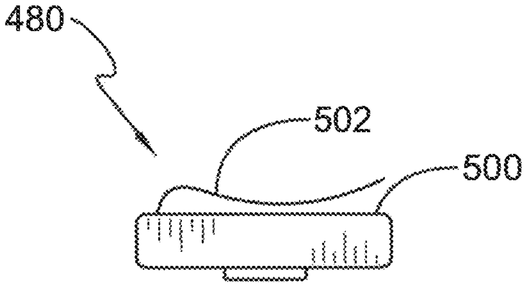
Figure 20:
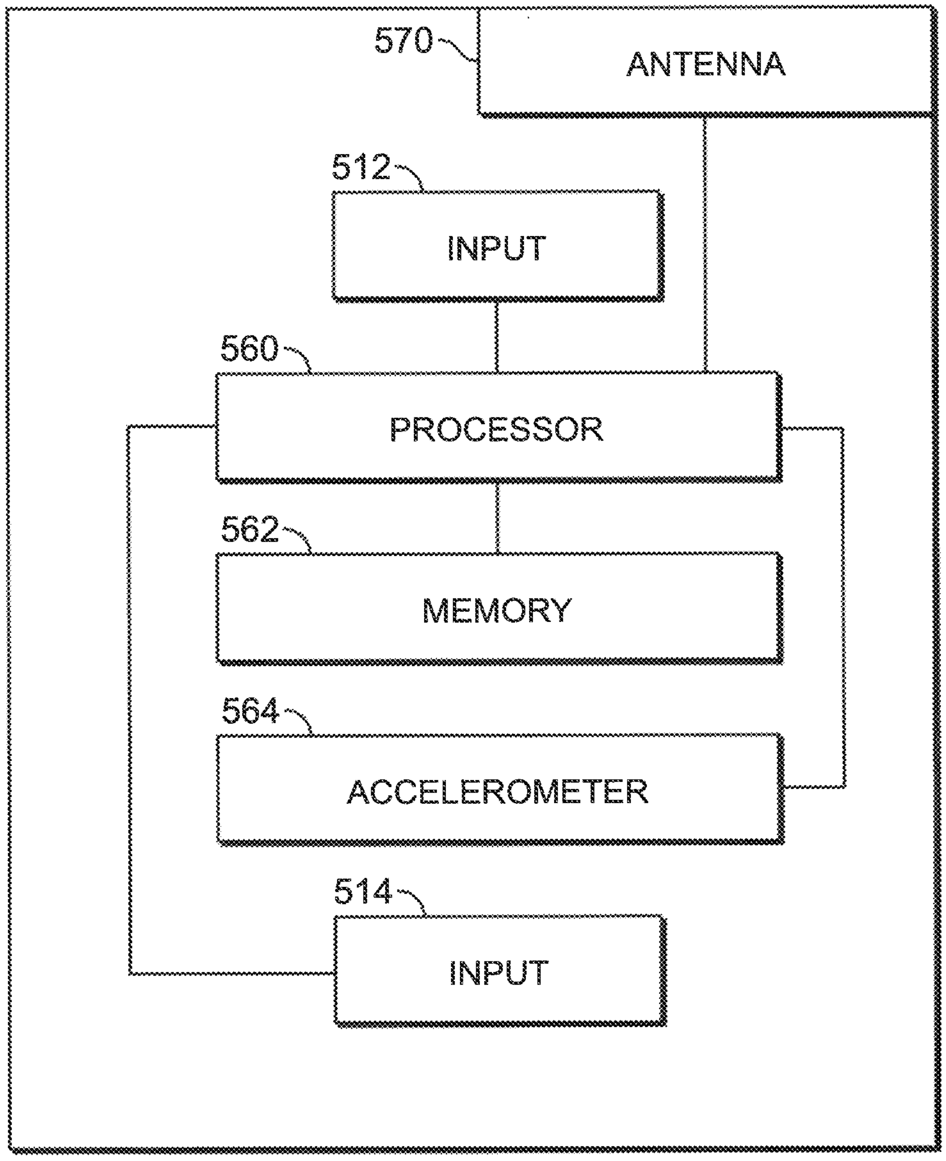
Figure 21:
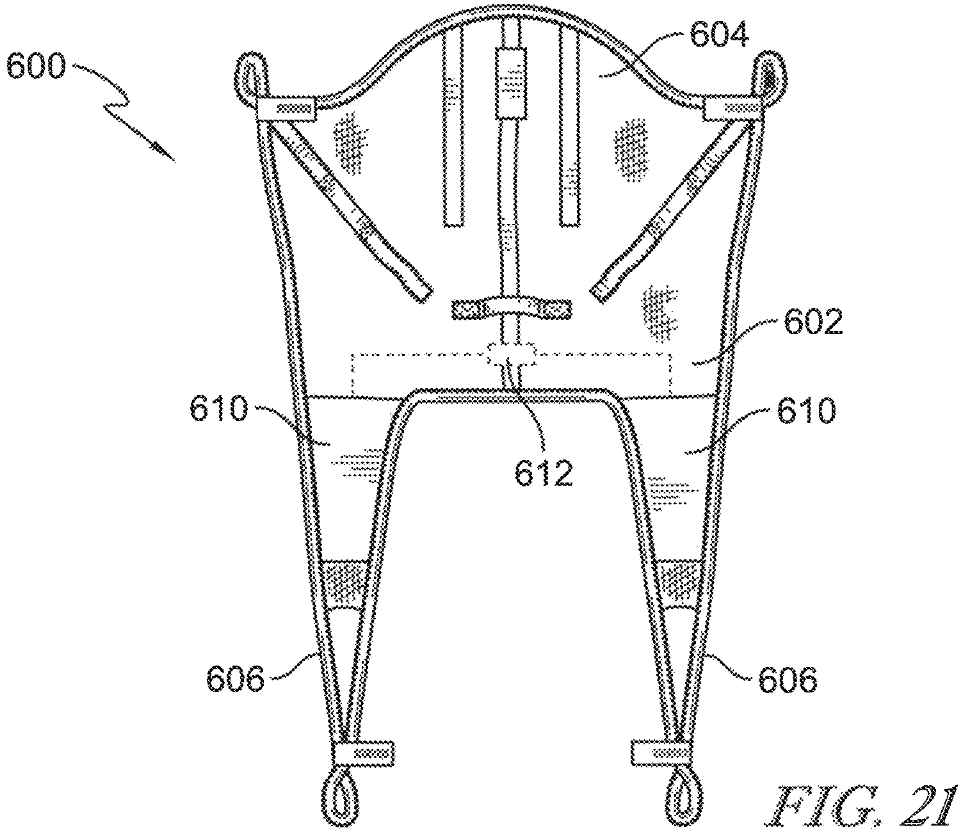
Figure 22:
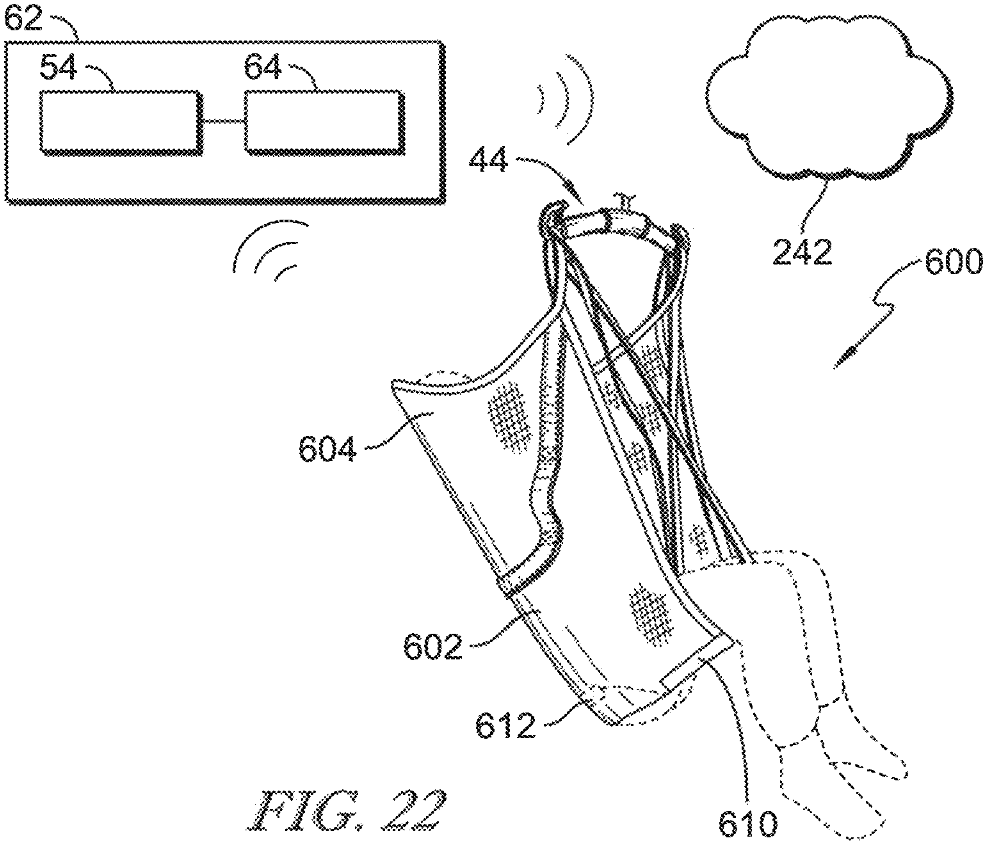

2 so that when the lift system controller is unclipped from the sling, it can be stored adjacent to the sling bar;

FIG. 17 is a front elevation view of an embodiment of a lift system controller of FIG. 15 showing up and down buttons at a top and bottom, respectively, of the lift system controller;

FIG. 18 is a top plan view of the lift system controller of FIG. 17 showing a profile of the clip that removably couples the lift system controller to the sling;

FIG. 19 is a front elevation view of an alternative embodiment of a lift system controller having a display located between the up and down buttons;

FIG. 20 is a diagrammatic view of circuitry of the lift system controller of FIGS. 15-18 showing the circuitry having an accelerometer to determine an orientation of the lift system controller so that a processor of the circuitry is able to determine which button is to be designated as the up button and which button is to be designated as the down button;

FIG. 21 is a top plan view of a sling, similar to FIG. 4, showing pressure sensors included in the leg sections of the sling; and FIG. 22 is a side perspective view of the sling of FIG. 21 showing the sling in use.

DETAILED DESCRIPTION

Although this disclosure refers to specific embodiments, it will be understood by those skilled in the art that various changes in form and detail may be made without departing from the subject matter set forth in the accompanying claims.

Figure 1:
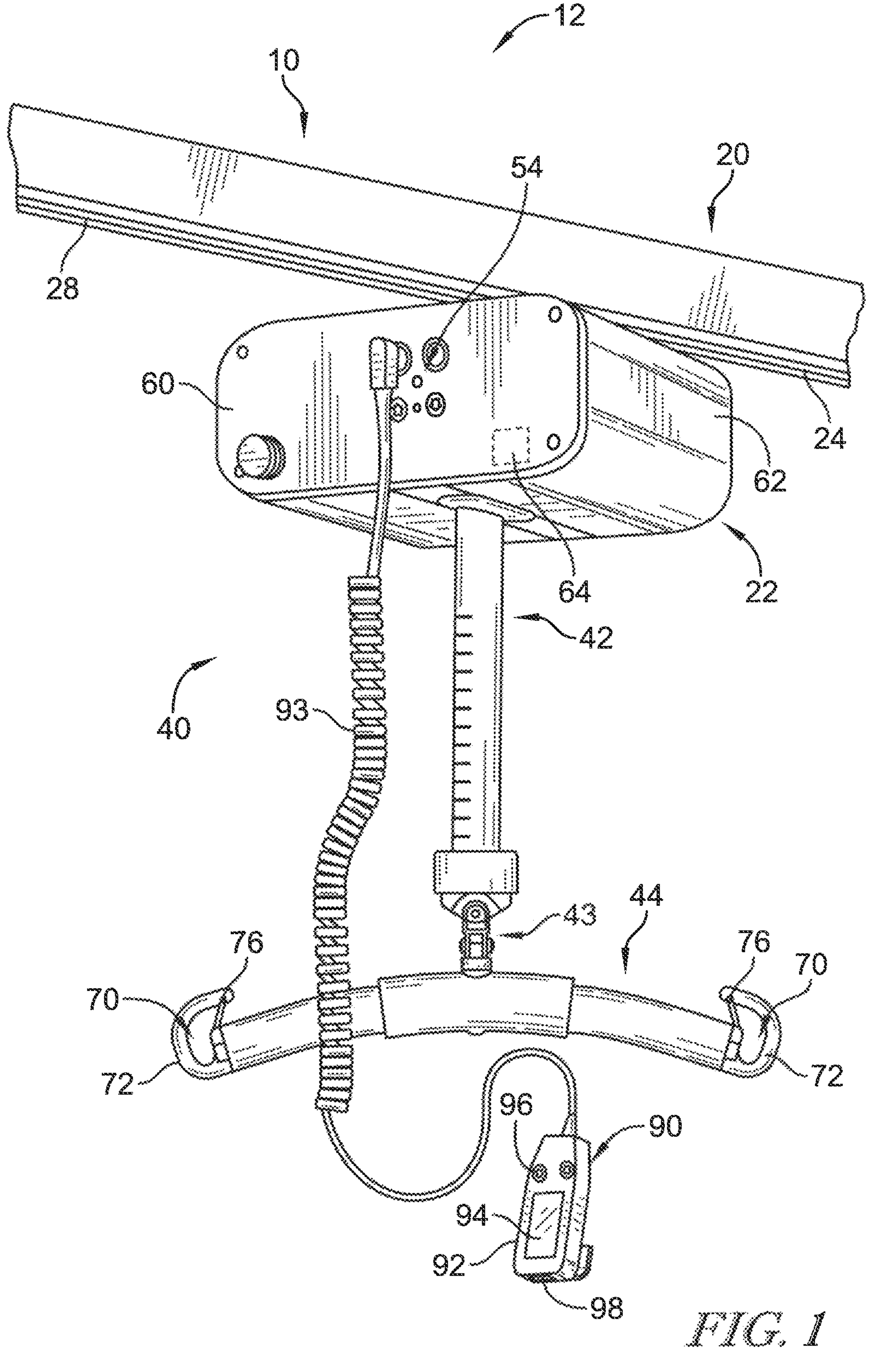
FIG. 1 is a front perspective view of an overhead patient lift system showing the patient lift system including an overhead support frame, a motor housing unit beneath the frame, a strap extending downwardly from the motor housing unit, a sling bar coupled to a lower end of the strap, and a handheld controller coupled to the motor housing unit by a coiled cable.

A patient lift system 10, according to one contemplated embodiment, is configured as an overhead patient lift system 12 as shown in FIG. 1. In some contemplated embodiments, the lift system 10 includes a mobile patient lift system 14 (e.g., a powered sit-to-stand lift or stand assist lift) shown in FIG. 2, or other person lifting devices. The lift system 12 of FIG. 1 includes an overhead rail 20 coupled to a ceiling of a room and a lift assembly 22 configured to move along the rail 20. Rail 20 is included as part of a frame of the lift system 12. Some such frames are floor supported and have upright stanchions and the like to which rail 20 is coupled, rather than having rail 20 fixed to the ceiling.

Illustrative rail 20 includes a track 24 and a conductor 28 extending along the track 24. In some embodiments, data and power are communicated over the conductor 28, thereby allowing a power source in the lift assembly 22 to be recharged, and also allows the lift assembly 22 to communicate with other devices such as the patient lift system 14, a communication system (not shown), and/or a hospital network (not shown). In some contemplated embodiments, portions of the rail 20 and lift assembly 22 are constructed as disclosed in U.S. Patent Application Publication No. 2012/0000876 A1, which is hereby incorporated herein by reference in its entirety to the extent not inconsistent with the present disclosure which shall control as to any inconsistencies.

The lift assembly 22 includes, a lift 40, a strap 42 configured to be extended and retracted by the lift 40, a sling bar 44 coupled to a lower end of the strap 42 by a coupler 43 such as a pin, latch, or hook, a sling 50 (shown in FIG. 3), and a control system 54 as shown in FIG. 1. The lift 40 includes a carriage 60 having a roller assembly (not shown) extending upwardly into an interior region of the rail 20 and configured to engage the track 24 of the rail 20 to permit the lift assembly 22 to be moved manually along the rail 20, a motor housing 62 coupled to the carriage 60, a motor 64 (shown diagrammatically) positioned in the housing 62 and configured to raise and lower the strap 42 by winding and unwinding the strap 42 on a drum (not shown). In some embodiments, the carriage 60 includes a conductor (not shown) configured to electrically couple with the conductor 28 on the rail 20.

Figure 3:
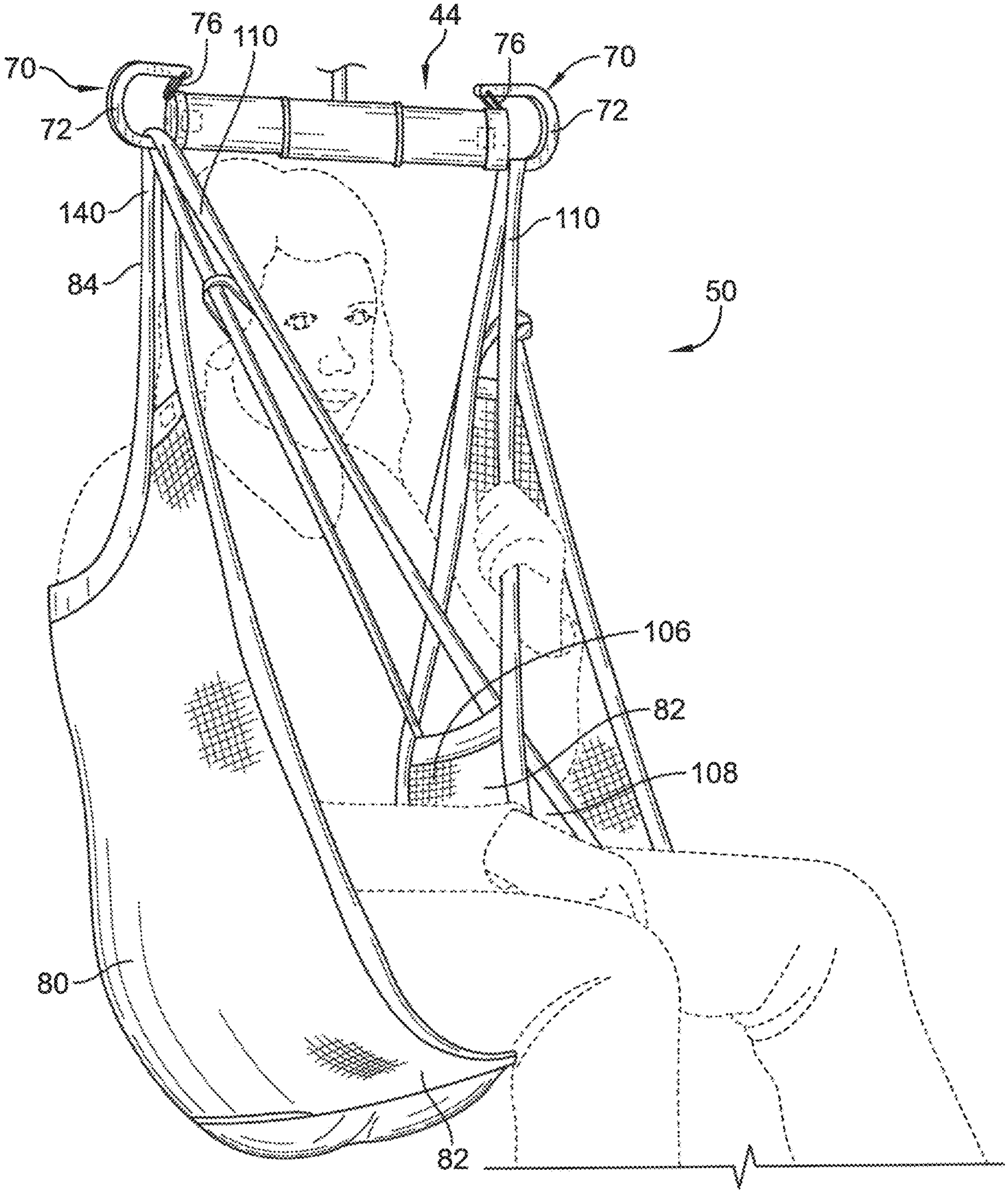
FIG. 3 is a front perspective view of a sling having loops attached to first and second hooks of the sling bar of one of the patient lift systems of FIG. 1 and FIG. 2.

The sling bar 44 is coupled to the end of the strap 42 and includes arms 70 with sling attachment hooks 72 at the ends of the arms 74. The sling attachment hooks 72 are configured to receive and removably retain loops of the sling 50. The sling attachment hooks 72 include a retaining element 76 that is configured to prevent the sling 50 from disengaging the attachment hooks 72. The retaining element 76 includes a spring loaded bail, finger, rod, post, or the like that is normally held in a closed position under the spring bias but that is movable to an open position during attachment of the loops of the sling 50 onto the respective hook 72. In use, the retaining elements 76 prevent the loops of the sling 50 from inadvertently moving off of the respective hooks 72. The sling 50 is used to support the person being moved by the lift assembly 22 and includes a main body portion 80, leg portions 82, and connecting straps 84 as shown in FIGS. 3 and 4. In some embodiments, the sling 50 can be one of the slings sold by Liko AB of Lulea, Sweden, such as, the Solo HighBack model 25 sling as shown in FIG. 3.

The control system 54 includes a user interface 90 having a handheld pendant 92 with a display 94 and buttons 96. A coiled cable 93 electrically couples the pendant 92 to the circuitry within the housing 62 of lift assembly 22. The buttons 96 provide input indicative of a user's desire to raise and lower the sling 50, and the display 94 is configured to display information related to the lift system 10, the patient, the room, the facility, and other information. In some contemplated embodiments, the pendant 92 includes an accelerometer 98 that is configured to determine when the pendant's 92 orientation has changed such that the button 96 that normally causes the lift 40 to raise the person upwardly is pointing downward, and re-assign the button function to the button 96 that is currently pointing upwardly, so that when a user presses the button 96 that appears to make the lift 40 raise the person, the lift 40 will, in fact, raise the person (instead of lower). In some contemplated embodiments, a battery of the pendant 92 is charged when the pendant 92 is docked in a docking station (not shown). In another contemplated embodiment, the battery is charged via the conductor 28 on the rail 20. In other contemplated embodiments, the battery is recharged over an Ethernet connection or over a communication bus.

Figure 2:
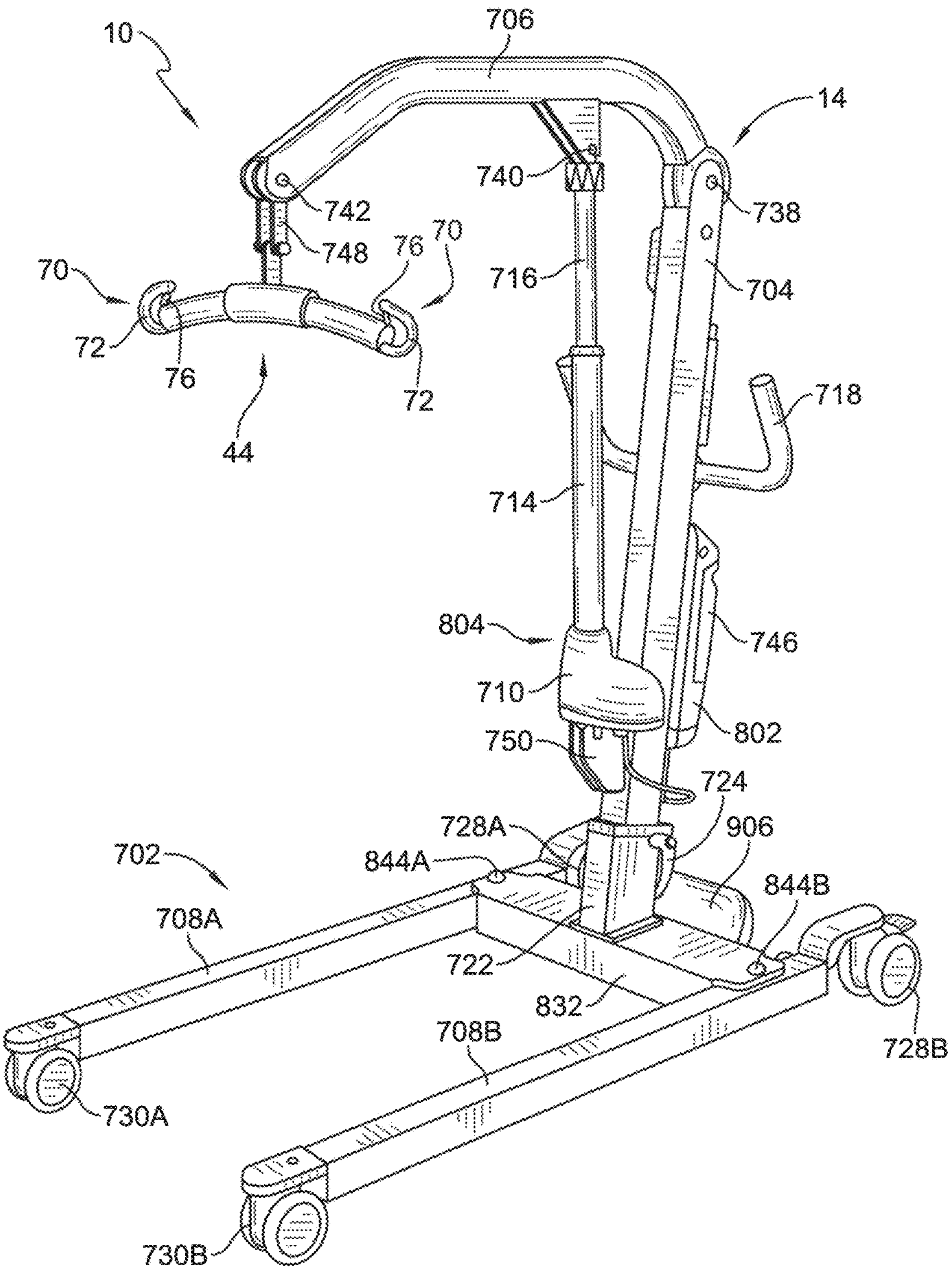
FIG. 2 is a front perspective view of a mobile patient lift system showing the mobile patient lift system including a frame having a base with a set of casters, a generally vertical mast extending upwardly from the base, and a support arm extending from the mast to overlie a space defined between a pair of base frame members, the mobile patient lift system also having a sling bar coupled to an end of the support arm spaced from the mast and a linear actuator extending between a lower region of the mast and the support arm.

Referring now to FIG. 2, the mobile patient lift system 14 includes a base 702, a lift mast 704 and a lift arm 706. The base 702 includes a pair of base legs 708A, 708B which are pivotally attached to a cross support 832 at base leg pivots 844A, 844B such that the base legs 708A, 708B are pivotally adjustable with respect to the lift mast 704. The base legs 708A, 708B may be pivoted with the base actuator 906 which is mechanically coupled to both base legs 708A, 708B. For example, in the configuration shown in FIG. 2, when the actuator 906 is raised, the base legs 708A and 708B are pivoted towards one another into a generally parallel orientation as shown in FIG. 2 and, when the actuator 906 is moved downwardly, the base legs 708A and 708B are pivoted away from one another into a spread orientation (not shown). The base legs 708A, 708B additionally include a pair of front casters 730A, 730B and a pair of rear casters 728A, 728B. The rear casters 728A, 728B have caster brakes in some embodiments.

In the illustrative embodiment, the base 702 may further comprise a mast support 722 disposed on the cross support 832. The mast support 722 is configured as a rectangular receptacle configured to receive the lower end of the lift mast 704 therein. The lower end of the lift mast 704 is secured with a pin, threaded fastener, or a similar fastener coupled to an adjustment handle 724. The pin or threaded fastener extends through the mast support 722 and into a corresponding hole(s) (not shown) in the lift mast 704. The lift mast 704 further includes at least one handle 718. The handle 718 provides an operator with a grip for moving the lifting device 14 on the casters 728A, 728B, 730A, 730B.

The lift arm 706 of patient lift system 14 is pivotally coupled to the lift mast 704 at the lift arm pivot 738 at an upper end of the lift mast 704 such that the lift arm 706 may be pivoted (e.g., raised and lowered) with respect to the base 702. The sling bar 44 is coupled to the lift arm 106 with an attachment coupling 748. In the embodiment shown in FIG. 2, the attachment coupling 748 is pivotally attached to the lift arm 706 at a distal end of the lift arm 706 opposite the lift arm pivot 738. In the illustrative embodiment, the attachment coupling 748 is pivotally attached to the lift arm 706 at attachment pivot 742 such that the sling bar may be pivoted with respect to the lift arm 706. However, it should be understood that, in other embodiments, the attachment coupling 748 may be fixedly attached to the lift arm 706 or the sling bar 44 may be directly coupled to the lift arm 706 without the use of an attachment coupling 748.

In the illustrative embodiment, the patient lift system 14 is a mechanized lift system. Accordingly, raising and lowering the lift arm 706 with respect to the base 702 is achieved using an actuator such as a lift actuator 804. In the embodiments shown, the lift actuator 804 is a linear actuator which includes a motor 710 mechanically coupled to an actuator arm 714. More specifically, the motor 710 includes a rotating armature (not shown) and the actuator arm 714 includes a threaded rod (not shown) coupled to the armature such that, when the armature is rotated, the threaded rod rotates and moves a nut (not shown) therealong to extend or retract an output shaft 716 relative to the actuator arm 714. Extension and retraction of the output shaft 716 causes lift arm 706 to pivot relative to mast 704.

In some embodiments, the lift actuator 804 further includes one or more limit switches coupled to the actuator arm 714. For example, the actuator arm 714 may comprise an upper limit switch (not shown) and a lower limit switch (not shown) which are mechanically coupled to the actuator arm 714 and electrically coupled to a control unit 802. The upper limit switch provides the control unit 802 of the lift system 14 with an electrical signal indicating that the output shaft 716 is fully extended (i.e., at an upper end position) while the lower limit switch provides the control unit 802 with an electrical signal indicating that the output shaft 716 is fully retracted (i.e., at a lower end position).

In the embodiment shown in FIG. 2, the lift actuator 804 is pivotably mounted on the lift mast 704 and pivotably coupled to the lift arm 706. In particular, the lift mast 704 comprises a bracket 750 to which the motor 710 of the lift actuator 204 is pivotably attached while the output shaft 716 is pivotably coupled to the lift arm 706 at an actuator pivot 740. Accordingly, it should be understood that, by actuating the lift actuator 804 with the motor 710, the output shaft 716 is extended or retracted thereby raising or lowering the lift arm 706 relative to the base 702. In some embodiments, the lift actuator 804 may further comprise an emergency release (not shown) which facilitates the manual retraction of the output shaft 716 in the event of a mechanical or electrical malfunction of the lift actuator 804.

Still referring to FIG. 2, the control unit 802 of the patient lift system 14 further includes a battery 746 that is electrically coupled to the lift actuator 804. The control unit 802 is operable to receive inputs from an operator via a control device coupled to the control unit 802. The control device may comprise a wired controller and/or one or more wireless controllers. For example, in some embodiments, the control device is a wired controller similar to user interface 90 of FIG. 1 or, alternatively, a controller integrated into the control unit 802. In other embodiments, the controller may be a wireless controller such as a wireless handheld controller like those discussed herein in connection with FIGS. 10-20. Based on the input received from the control device, the control unit 802 is programmed to adjust the position of the lift arm 706 by sending electric control signals to the lift actuator 804.

Referring now to FIG. 4, the sling 50 includes the main body section 80 configured to retain the back of a patient when the patient is held in the sling 50. A pair of leg sections 82 extends from the main body section 80 and includes a right leg section 106 configured to hold the patient's right leg and a left leg section 108 configured to hold the patient's left leg. Each leg section 82 extends from the main body section 80 to an end 110. The end 110 of each leg section 82 includes an attachment loop 120. The attachment loop 120 may be formed from fabric of the sling that is shaped in a loop configuration. The fabric is formed from a high strength material that can retain a weight of the patient. In some embodiments, the attachment loop 120 may be formed from a metal hoop or loop that is coupled to the end 110 of the leg section 82.

A back section 130 extends from the main body section 80 and is configured to position against the patient's back when the patient is held in the sling 50. The back section 130 extends from the main body section 80 to an end 132. The end 132 has corners 134 including a right corner 136 that is on the same side of the sling 50 as the right leg section 106 and a left corner 138 that is on the same side of the sling 50 as the left leg section 108. Each corner 134 includes an attachment loop 140. The attachment loop 140 may be formed from fabric of the sling that is shaped in a loop configuration. The fabric is formed from a high strength material that can retain a weight of the patient. In some embodiments, the attachment loop 140 may be formed from a metal hoop that is coupled to the corner 134 of the back section 130.

The right leg section 106 includes a short range wireless tag 150 that is configured to transmit a unique identification signal. The tag 150 may be a radio-frequency identification (RFID) tag or a near field communication (NFC) tag. The tag 150 is positioned adjacent the attachment loop 120 of the right leg section 106. The tag 150 may be sewn into the sling 50 or attached to an outer surface of the sling 50. As described in more detail below, the tag 150 is configured to transmit the unique identification signal to an electronic reader.

The left leg section 108 includes a short range wireless tag 152 that is configured to transmit a unique identification signal different than the signal transmitted by the tag 150. The tag 152 may be an RFID tag or an NFC tag. The tag 152 is positioned adjacent the attachment loop 120 of the left leg section 108. The tag 152 may be sewn into the sling 50 or attached to an outer surface of the sling 50. As described in more detail below, the tag 152 is configured to transmit the unique identification signal to an electronic reader.

The right corner 136 includes a short range wireless tag 154 that is configured to transmit a unique identification signal different than the signal transmitted by the tags 150 and 152. The tag 154 may be an RFID tag or an NFC tag. The tag 154 is positioned adjacent the attachment loop 140 of the right corner 136. The tag 154 may be sewn into the sling 50 or attached to an outer surface of the sling 50. As described in more detail below, the tag 154 is configured to transmit the unique identification signal to an electronic reader.

The left corner 138 includes a short range wireless tag 156 that is configured to transmit a unique identification signal different than the signal transmitted by the tags 150, 152, and 154. The tag 156 may be an RFID tag or an NFC tag. The tag 156 is positioned adjacent the attachment loop 140 of the left corner 138. The tag 156 may be sewn into the sling 50 or attached to an outer surface of the sling 50. As described in more detail below, the tag 156 is configured to transmit the unique identification signal to an electronic reader. Illustrative sling 50 has a handle 157 in a central region of main body section 80 and a pair of handles 159 provided by portions of somewhat diagonally extending reinforcement strips in back section 130. Handles 157, 159 are gripped by a caregiver attending to the patient being lifted to help maneuver the patient as desired while the patient is supported by the respective lift system 12, 14. Sling 50 also has a pocket 161 in which pendant 92 can be stored, as desired, when not in use.

When attached to the hooks 72 of sling bar 44, the leg sections 82 of sling 50 are crisscrossed in between the patients legs, as shown in FIG. 3, so that loop 120 having tag 152 is coupled to the same hook 72 as loop 140 having tag 154 and so that loop 120 having tag 150 is coupled to the same hook as loop 140 having tag 156. The attachment of sling 50 to sling bar 44 in this manner safely retains the patient on sling 50 during raising and lowering by the respective patient lift system 12 or patient lift system 14 as the case may be.

Figure 5:
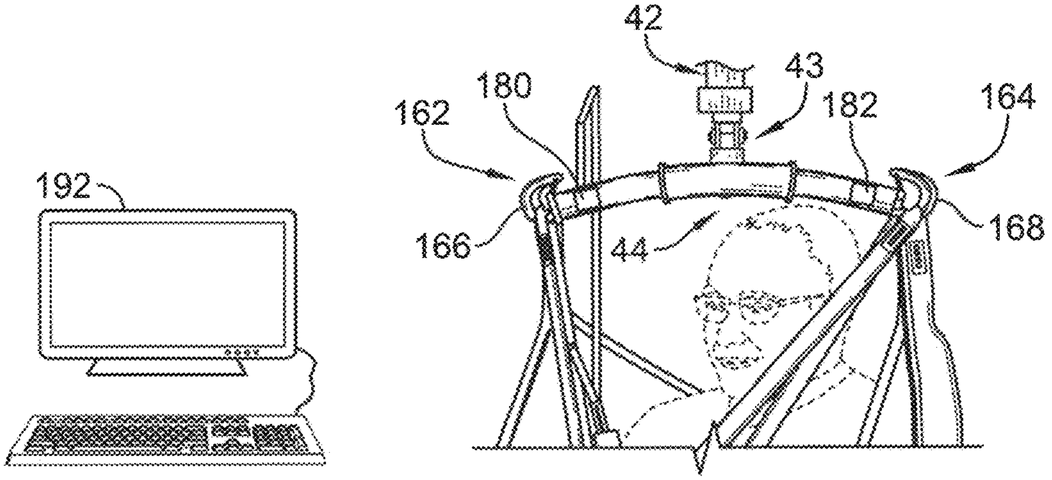
FIG. 5 is a front perspective view of a detection system for determining whether the sling shown in FIG. 4 is properly attached to the sling bar of the overhead patient lift system of FIG. 1 showing first and second electronic readers attached to an external surface of the sling bar adjacent respective hooks of the sling bar for reading electronic tags included in the loops of the sling and showing a remote device, such as a computer, to track lift system and sling usage based on information from the first and second electronic readers.

Referring now to FIG. 5, the sling bar 44 includes a right end 162 and a left end 164. A right attachment hook 166 is positioned on the right end 162 and a left attachment hook 168 is positioned on the left end 164. The right attachment hook 166 is configured to couple to the attachment loop 120 of the left leg section 108 and the attachment loop 140 of the right corner 136. The left attachment hook 166 is configured to couple to the attachment loop 120 of the right leg section 106 and the attachment loop 140 of the left corner 138. By attaching the attachment loops 120 and 140 to the respective attachment hook 166, 168, the sling 50 is retained on the sling bar 44. That is, a patient may be positioned in the sling 50 and raised and lowered by activating the motor 64 of the lift assembly 22.

The right end 162 of the sling bar 44 includes an electronic reader 180 and the left end 164 of the sling bar 44 includes an electronic reader 182. The electronic readers 180, 182 may be any device capable of receiving an identification signal from a short range wireless tag. The electronic readers 180, 182 may be coupled to an outer surface of the sling bar 44 thereby permitting existing sling bars 44 without electronic readers 180, 182 to be upgraded to sling bars 44 having electronic readers 180, 182. In some embodiments, the electronic readers 180, 182 are positioned within an interior region of the sling bar 44 and capable of receiving signals through the sling bar 44.

The electronic reader 180 is configured to identify the tags 152 and 154 to ensure that the left leg section 108 and the right corner 136 are properly attached to the right attachment hook 166. When the electronic reader 180 identifies the tags 152 and 154, the electronic reader 180 communicates with the control system 54 of the lift system 10 so that the operation of the motor 64 remains enabled. That is, if tags other than tags 152, 154 are detected or read by the reader 180, the motor 64 is disabled from operation by the control system 54. When disabled, the motor 64 is not powered for operation. Additionally, if a tag mismatch such as tag 150 and tag 154, or such as tag 152 and tag 156, are identified by the electronic reader 180 as being the pair of tags having loops 120, 140 attached to the respective hook 166, the motor 64 is disabled and prohibited from operating.

The electronic reader 182 is configured to identify the tags 150 and 156 to ensure that the right leg section 106 and the left corner 138 are properly attached to the left attachment hook 168. When the electronic reader 182 identifies the tags 150 and 156, the electronic reader 182 communicates with the control system 54 of the lift system 10 so that the operation of the motor 64 remains enabled. That is, if tags other than tags 150, 156 are detected or read by the reader 182, the motor 64 is disabled from operation by the control system 54. When disabled, the motor 64 is not powered for operation. Additionally, if a tag mismatch such as tag 150 and tag 154, or such as tag 152 and tag 156, are identified by the electronic reader 182 as being the pair of tags having loops 120, 140 attached to the respective hook 168, the motor 64 is disabled and prohibited from operating.

In the discussion above, it was assumed that the loops 120, 140 having tags 152, 154 should be coupled to hook 166 of sling bar 44 and read by reader 180 and that loops 120, 140 having tags 150, 156 should be coupled to hook 168 of sling bar 44 and read by reader 182. However, it is possible that a caregiver may wish to attach sling 50 to sling bar 44 in the reverse arrangement. That is, sling 50 may also be properly attached to sling bar so that reader 180 identifies tags 150, 156 and reader 182 identifies tags 152, 154. Thus, as long as the proper tag pairs (e.g., tags 150, 156 and tags 152, 154) are read by respective readers 180, 182 the sling 50 is considered to be properly attached to the sling bar 44.

The electronic readers 180 and 182 may also be in communication with a remote device 192, for example a computer at a nurse's station or a computer elsewhere in the healthcare facility. Other examples of remote devices 192 include smart phones, tablet computers, personnel digital assistants (PDA's) and the like. The remote device 192 tracks a number of times that the electronic readers 180, 182 identify the tags 150, 152, 154, and 156 to track a number of times that the sling 50 is in use. By tracking the usage of the sling 50, the healthcare facility may determine whether a sling 50 should be replaced or whether additional slings 100 are needed at the healthcare facility.

The remote device 192 may also have an alarm that notifies a caregiver when the sling 50 is improperly attached to the sling bar 44. By alerting the caregiver, the caregiver is notified that the sling 50 is improperly attached to the sling bar 44 and prompted to correct the attachment of the sling 50. Additionally, in a scenario where the motor 64 is not deactivated, injury to the patient may be avoided by alerting the caregiver that the sling 50 is improperly attached. Thus, the remote device 192 may be carried by the caregiver while the caregiver is in the patient room attempting to operate the patient lift system 10.

Figure 6:
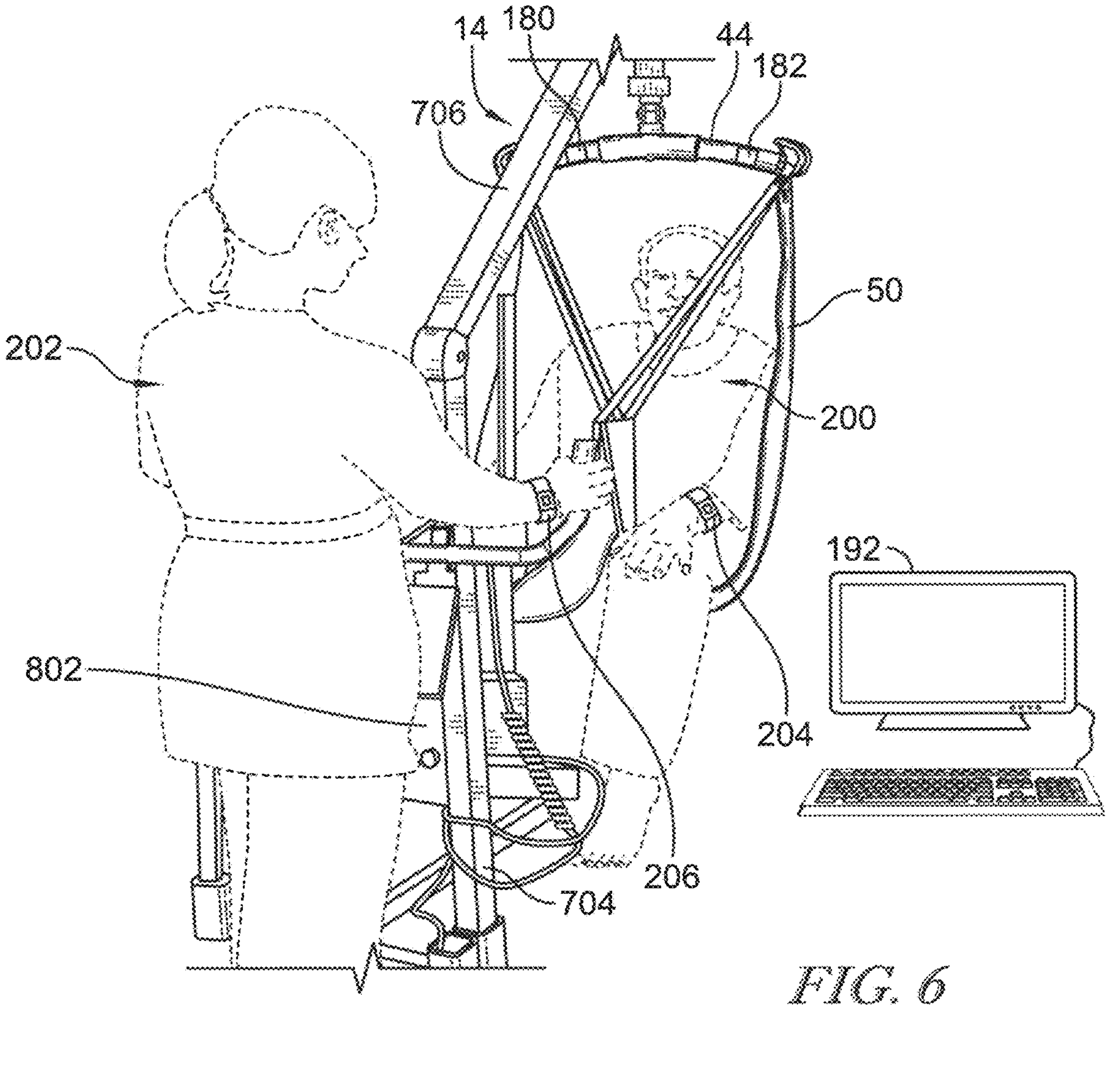
FIG. 6 is a front perspective view of the detection system for determining whether the sling shown in FIG. 4 is properly attached to the sling bar of the mobile patient lift system of FIG. 2 showing the first and second electronic readers for reading the electronic tags in the loops, showing the remote device, and showing wireless tags worn by a patient and a caregiver for communication with one or both of the electronic readers of the sling bar.

As illustrated in FIG. 6, the sling 50 is configured to retain a patient 200 while being operated by a caregiver 202. In the illustrative embodiment, the patient 200 is wearing a device having a short range wireless tag 204. The tag 204 may be an RFID tag. For example, the tag 204 may be incorporated into a wristband or other wearable item. The tag 204 transmits a unique identification signal that may be read by the electronic reader 180 and/or the electronic reader 182. In some embodiments, the sling bar 44 includes a unique electronic reader that reads the identification signal from the tag 204. In some embodiments, operation of the motor 64 is prohibited until the patient is identified by reading the identification signal from the tag 204. In some embodiments, a patient identification is entered into the lift system 10 prior to supporting the patient 200 on the sling 50. Accordingly, if the unique identification signal from the tag 204 does not match the patient identification entered into the lift system 10, operation of the motor 64 is disabled.

Also, the caregiver 202 may be wearing a device having a short range wireless tag 206. The tag 206 may be an RFID tag. For example, the tag 206 may be incorporated into a wristband or other wearable item or clipped onto the caregiver's clothing. The tag 206 transmits a unique identification signal that may be read by the electronic reader 180 and/or the electronic reader 182. In some embodiments, the sling bar 44 includes a unique electronic reader that reads the identification signal from the tag 206. In some embodiments, operation of the motor 64 is prohibited until the caregiver is identified by reading the identification signal from the tag 206. In some embodiments, a caregiver identification is entered into the lift system 10 prior to supporting the patient 200 on the sling 50. Accordingly, if the unique identification signal from the tag 206 does not match the caregiver identification entered into the lift system 10, operation of the motor 64 may be disabled.

Signals may be sent to the remote device 192 when the patient 200 or the caregiver 202 is identified. Accordingly, the remote device 192 may track which patient 200 is using the lift system 10 and which caregiver 202 is operating the lift system 10. In some embodiments, if the wrong patient 200 is identified, an alarm may be triggered by the remote device 192 or the lift system 10. Additionally, if an unauthorized caregiver 202 is identified, the alarm may be triggered. It is also within the scope of this disclosure for the motor 64 to be disabled if the wrong patient 200 or caregiver 202 is identified. Thus, in some embodiments, the remote device 192 includes a database of caregivers who have been properly trained and are qualified to operate the lift system 10. The remote device 192 also may include patient information, such patient weight. The remote device 192 communicates with the control system 54 of the patient lift system 10 as to whether the motor 64 should be enabled or disabled in some embodiments.

The embodiments shown in FIGS. 5 and 6 include various checks to determine whether the lift system 10 is being operated correctly. For example, the lift system 10 may be disabled unless at least one of the caregiver 202 is properly identified, the patient 200 is properly identified, or the sling 50 is properly oriented on the sling bar 44. In some embodiments, the lift system 10 is disabled unless at least two of the caregiver 202 is properly identified, the patient 200 is properly identified, or the sling 50 is properly oriented on the sling bar 44. In some embodiments, the lift system 10 is disabled unless all of the caregiver 202 is properly identified, the patient 200 is properly identified, and the sling 50 is properly oriented on the sling bar 44.

Figure 7:
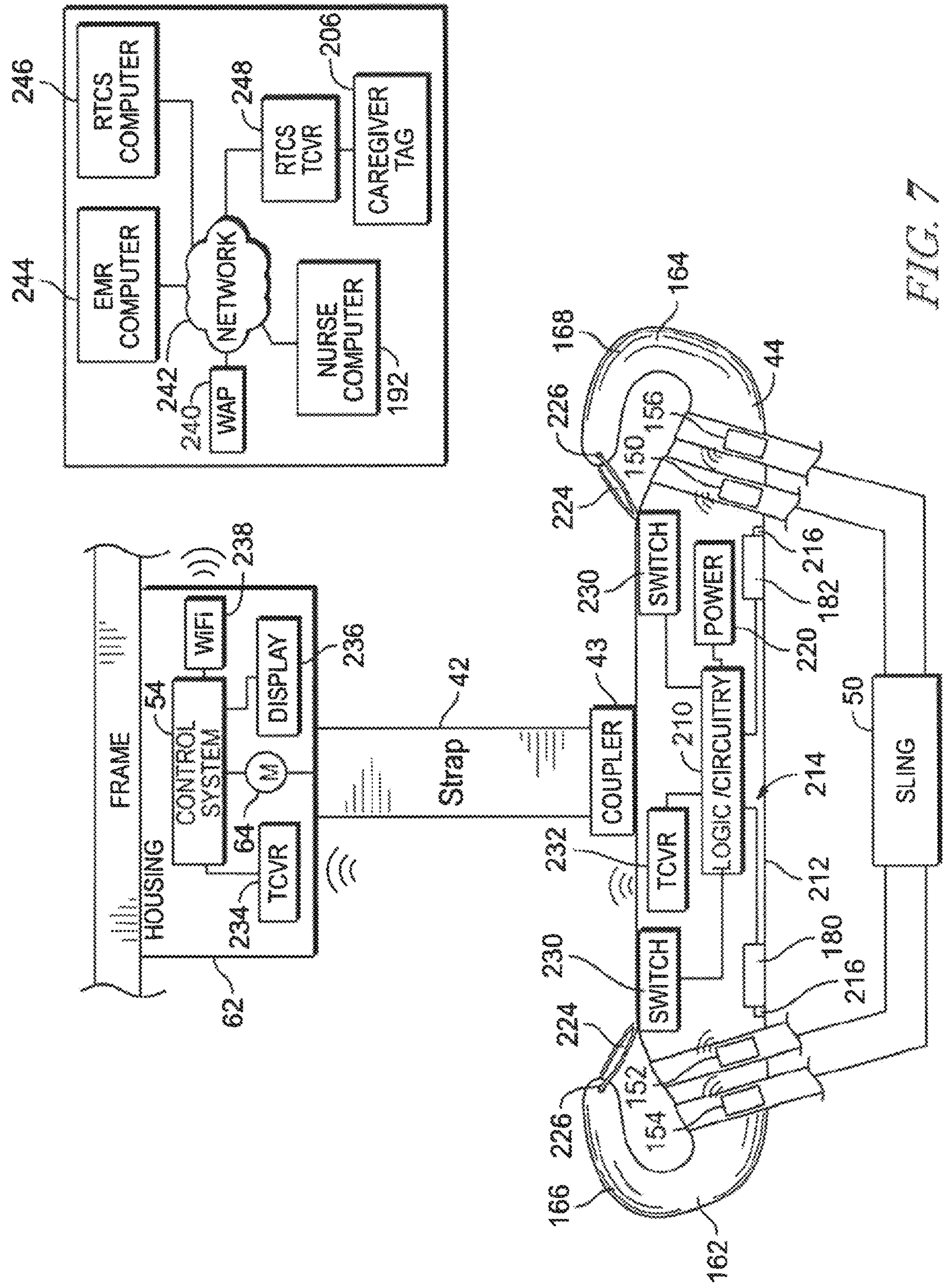
FIG. 7 is a diagrammatic view of showing the detection system having circuitry inside the sling bar including first and second electronic readers in wireless communication with tags in the loops of the sling and in wireless communication with circuitry in a housing of the motor housing unit and showing the circuitry in the housing communicating with a network of a healthcare facility via a wireless access point (WAP)

Referring now to FIG. 7, electronic reader 180 and electronic reader 182 are illustrated inside the sling bar 44 and coupled to control circuitry 210. The sling bar 44 includes a wall 212 that defines a cavity 214. The electronic readers 180, 182 are positioned within the cavity 214. In such an embodiment, the electronic readers 180, 182 are capable of receiving identification signals from a tag, for example, tags 150, 152, 154, and 156, through the wall 212 of the sling bar 44. The electronic readers 180, 182 include an antenna 216 that receives the identification signals. In the illustrated embodiment, the antenna 216 is positioned within the cavity 214 and receives the identification signals through the wall 212. In other embodiments, the antenna 216 extends through the wall 212 and is positioned outside of the sling bar 44.

A power source 220 is positioned within the cavity 214 to power the electronic readers 180, 182 in the illustrative embodiment. In other embodiments, the electronic readers 180, 182 are powered by an external power source that is coupled to the respective electronic reader 180, 182 via cables or wires extending into the cavity 214. For example, such cables or wires may be integrated into or otherwise coupled to strap 42 and extend from the strap 42 into the cavity 214. The power source 220 may provide continual power to the electronic readers 180, 182. In other embodiments, the electronic readers 180, 182 are only powered when the sling 50 is in use, as described below.

Right attachment hook 166 and left attachment hook 168 are positioned at the ends of the sling bar 44 as noted in the above discussion. The attachment hooks 166, 168 each include a clip 224 that is attached to the sling bar 44 at a hinge 226. The clip 224 is configured to move between an open and closed position (illustrated). When the loop, for example loop 120 or 140, is coupled to the sling bar 44, the clip 224 moves into the open position to allow the loop to be coupled to the respective attachment hook 166, 168. Clips 224 were referred to as retaining elements 76 in connection with FIGS. 1-3.

A switch 230 is positioned within the cavity 214 and contacts the clip 224 when the clip 224 is in the closed position. The electronic readers 180, 182 are configured to be in a sleep mode when not in use. In response to the clip 224 being opened, the switch 230 sends a signal to the respective electronic reader 180, 182 indicating that a loop is being attached to the respective attachment hook 166, 168. The signal from the switch 230 prompts the respective electronic reader 180, 182 to wake up and draw power from the power source 220. Once powered, the electronic reader 180, 182 reads the identification signal from the tag. Accordingly, the lift system 10 saves power by only powering the electronic readers 180, 182 when the sling 50 is being attached to the sling bar 44.

The control circuitry 210 is configured to transmit a messages via a transceiver 232 to a transceiver 234 in the housing 62. The messages are delivered to the control system 54, which controls the motor 64. The messages indicate to the control system 54 whether the sling 50 is properly attached to the sling bar 44. Thus, control circuitry 210 includes a processor and memory that operate to implement the software logic to determine the proper attachment or improper attachment of sling 50 to sling bar 44. The motor 64 remains operational if the control system 54 receives a message from circuitry 210 via transceivers 232, 234 indicating that the sling 50 is properly attached to sling bar 44. On the other hand, if the control system 54 receives a message from circuitry 210 via transceivers 232, 234 that the sling 50 is not properly attached to the sling bar 44, the control system 54 prevents the motor 64 from operating. A display 236 is provided in some embodiments to show the status of the system 10 and to provide alert messages notifying the caregiver that the sling 50 is not properly attached to the sling bar 44.

The housing 62 may also include a WiFi transceiver 238 for wireless communication of control system 54 with a wireless access point 240 of a healthcare facility network 242. Control system 54 is labeled as controller 54 in FIG. 7. Controller 54 includes a processor and memory in which software for operating lift system 10 is stored. In the illustrative example, the network 242 is in communication with an electronic medical record (EMR) computer 244. Accordingly, the EMR computer 244 can track when the sling 50 is properly attached to the sling bar 44. In some embodiments, the network 242 communicates with a real time locating system (RTLS) computer 246, which tracks a location of the caregiver tag 206 using real time locating transceivers 248 situated throughout the healthcare facility to ensure that the proper caregiver 202 is present when the sling 50 is attached to the sling bar 44. In some embodiments, the network 242 also communicates with the remote device 192 which in FIG. 7 is labeled as nurse call computer 192.

Figure 8:
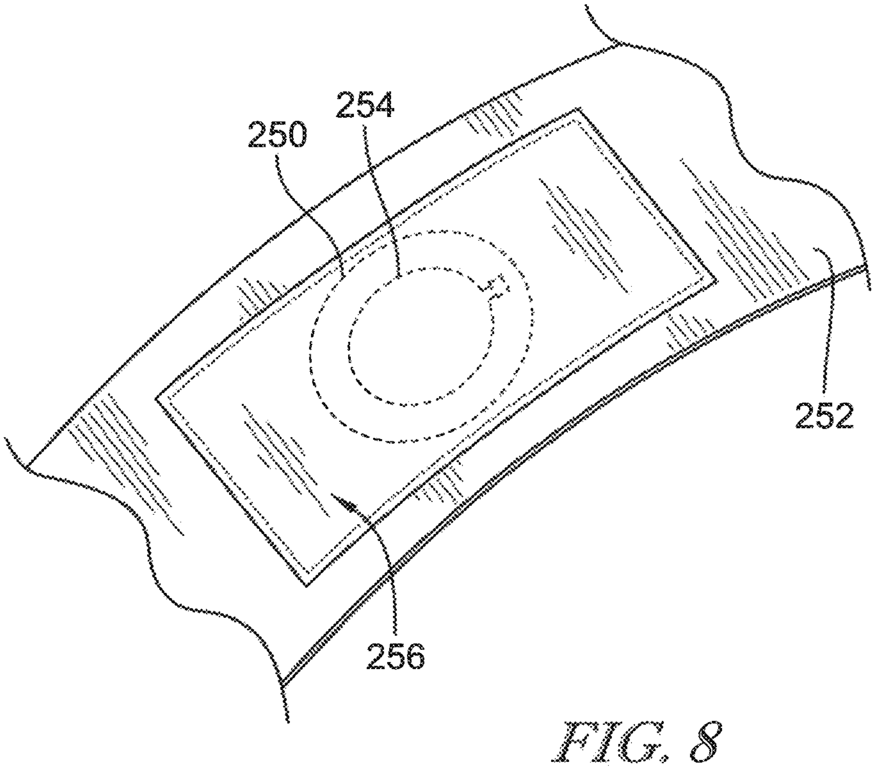
FIG. 8 is a top perspective view of a strap of the sling showing a wireless tag included in a label that is coupled by stitching to the strap.

As illustrated in FIG. 8, a short range wireless tag 250, for example tag 150, 152, 154, or 156, may be positioned on a strap 252 of the sling 50. The wireless tag 250 includes an antenna 254 that transmits the unique identification signal to an electronic reader, for example electronic reader 180 or electronic reader 182. The tag 250 may be sewn to the strap 252 or adhered with an adhesive, for example. A cover 256 is positioned over the tag 250. For example, the cover 256 may be a transparent plastic cover through which the identification signal is transmitted. In other embodiments, the cover 256 may be a fabric cover or label that is sewn over the tag 250 and allows the identification signal to be transmitted therethrough. In some embodiments, the wireless tag 250 is included in the label 256 that is coupled to the strap 252. Tag 250 is a passive RFID or NFC tag in some embodiments. Thus, wireless energy emitted by readers 180, 182 is used by the passive tag 250 to provide backscattered data, including the tag ID, back to the respective reader 180, 182 as reflected energy. In other embodiments, tag 250 is an active tag with its own power source.

Figure 9:
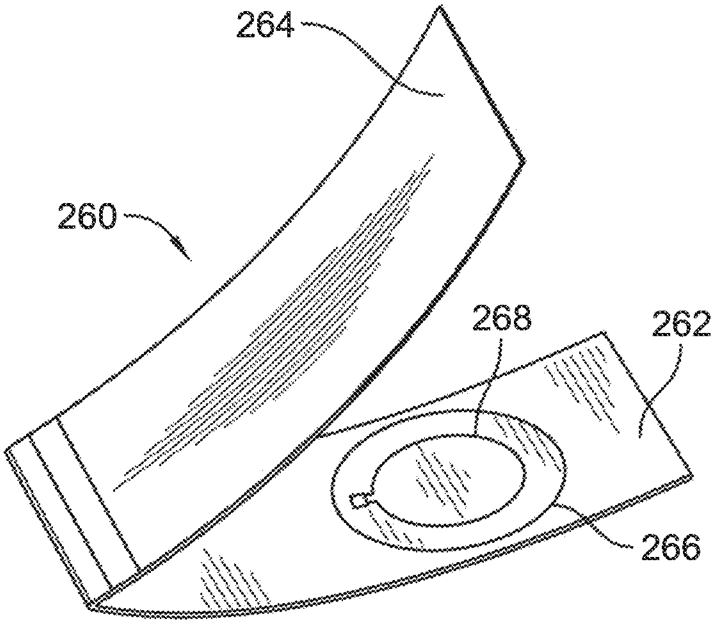
FIG. 9 is a top perspective view showing two layers of a strap of the sling opened up to expose a wireless tag positioned between the two layers of the strap.

FIG. 9 illustrates another embodiment of a strap 260 of the sling 50. The strap 260 includes an outer strap 262 and an inner strap 264 that are attached to each other under normal circumstances. A tag 266, for example tag 150, 152, 154, or 156, is sandwiched between the inner strap 264 and outer strap 262. In FIG. 9, the inner strap 264 and outer strap 262 are opened up so the tag 266 can be seen coupled to outer strap 262. It should be noted that the tag 266 may be coupled to the inner strap 264 in some embodiments. The tag 266 includes an antenna 268 that transmits the unique identification signal. The inner strap 264 is joined to the outer strap 262 so that the tag 266 is enclosed between the inner strap 264 and the outer strap 262. The antenna 268 is capable of transmitting the identification signal through the inner strap 264 and the outer strap 262. The discussion above of tag 250 of FIG. 8 is equally applicable to tag 268 of FIG. 9.

Figure 10:
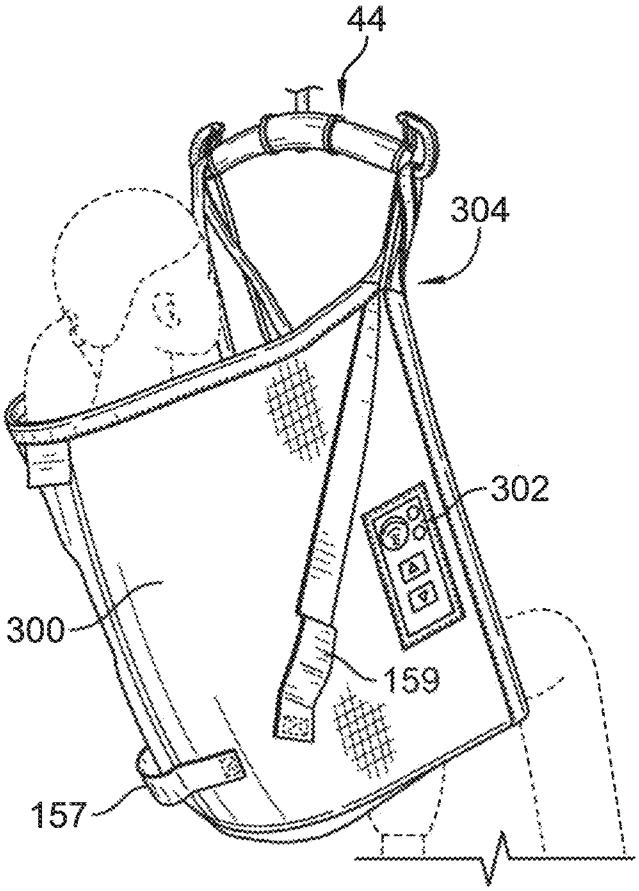
FIG. 10 is a rear perspective view of a sling in accordance with an embodiment of the present disclosure showing a control panel attached to the sling and having user inputs that are pressed to send wireless signals to the circuitry of the motor housing unit to control raising and lowering of the sling and the patient therein.

Referring now to FIG. 10, an embodiment of a sling 300 includes a control panel 302 that may be sewn to the fabric of the sling 300 or otherwise attached to the sling 300. In other embodiments, the control panel 302 may be embedded into the fabric of the sling 300, for example, in a pocket of the sling 300. The control panel 302 is illustrated in a corner 304 of the sling 300. In other embodiments, the control panel 302 is secured in other areas of the sling 300. It should be appreciated that any of the slings 50 disclosed herein may include control panel 302.

Figure 11:
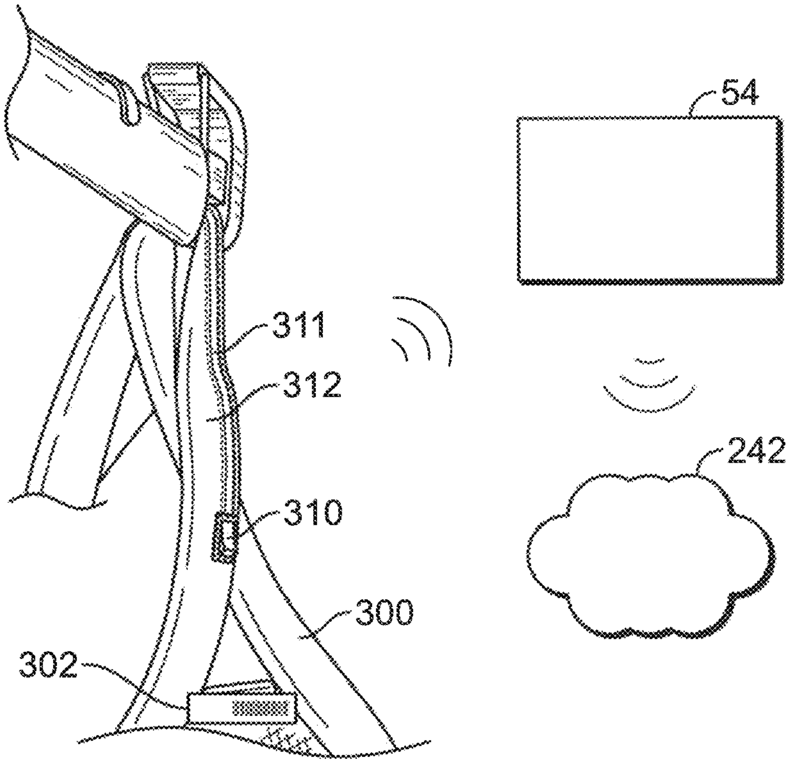
FIG. 11 is a rear perspective view of a portion of the sling of FIG. 10 showing an elongated spring extending along one of the loops of the sling and a switch located at a bottom end of the elongated spring, the switch being coupled to the control panel so that a load on the spring when the sling is in use changes the state of the switch which wakes up the control panel for wireless communication with a controller of the lift housing unit and increases a usage count for the sling.

As illustrated in FIG. 11, a switch 310 is coupled to the control panel 302 and is coupled to a spring 311 that extends along a strap 312 of the sling 300. The switch 310 detects when weight is applied to the sling 300 due to the spring 311 extending and activating the switch. That is, if a patient is positioned in the sling 300, the switch 310 is activated by the tension in spring 311. In some embodiments, the switch 310 wakes up control panel 302 so that control panel 302 is enabled for communication with control system 54 either directly or through the control circuitry 210. Thus, activation of switch 310 causes a power source of control panel 302 to turn on and permit the control panel 302 to provide inputs to the control system 54 to operate the motor 64 of the lift system 10. That is, the control panel 302 is not able to be used to operate the motor 64 until the switch 310 detects weight on the sling 300. In some embodiments, a predetermined weight is required to be detected on the sling 300 before the switch 310 is activated. For example, if the average patient weighs over 100 pounds, the switch 310 may require at least 100 pounds of weight to be activated. By setting a predetermined weight, false detections may be avoided, i.e. if the sling 300 is pulled on without a patient on the sling 300. In some embodiments, the control panel 302 monitors the number of times the switch 310 is activated to track a number of uses of sling 300. In some embodiments, the control panel 302 communicates through the control circuitry 210 and the control system 54 to send data to the network 242. In other embodiments, control panel 302 communicates with the network 242 only through control system 54 without involving control circuitry 210 as shown diagrammatically in FIG. 11.

Figure 12:
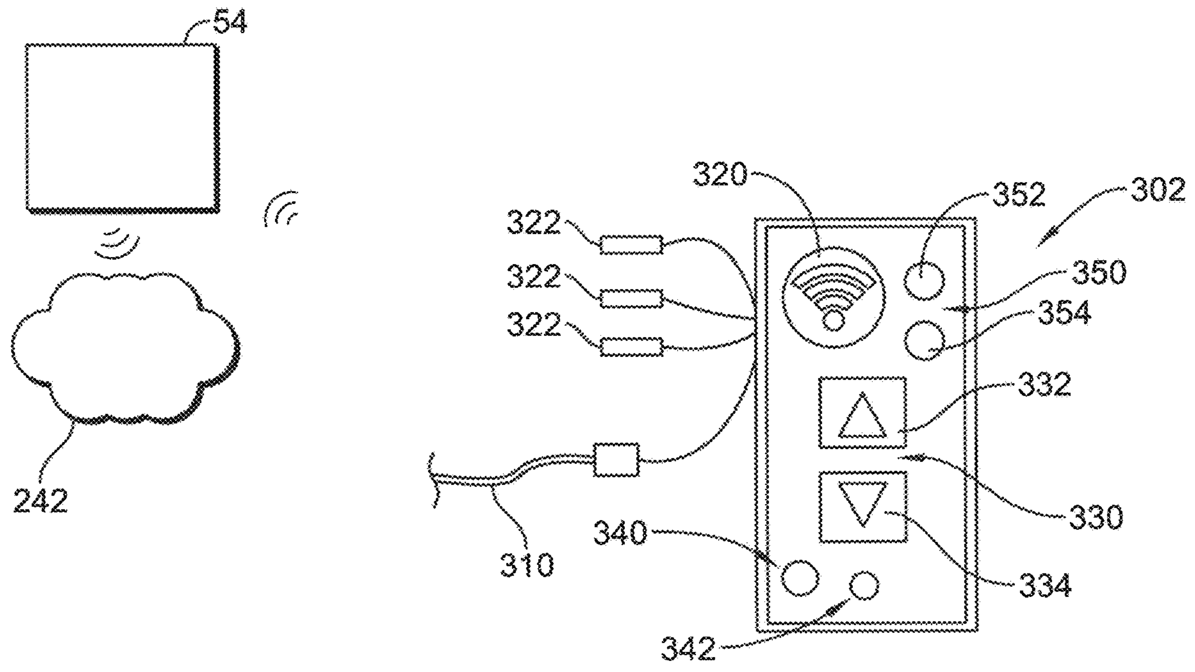
FIG. 12 is a diagrammatic view of the control panel of FIG. 10 showing three electronic readers for reading electronic tags wired to the control panel, the spring and switch of FIG. 11 wired to the control panel beneath the three electronic readers, and the control panel wirelessly communicating with the controller of the lift housing unit which, in turn, is in wireless communication with the network of the healthcare facility.

Referring now to FIG. 12, the control panel 302 is shown with the switch 310 extending therefrom. The control panel 302 also includes a wireless communicator 320 that is configured to send wireless messages to control system 54 of the patient lift system 10. In some embodiments, the tag 320 operates in a similar fashion as the tags described above. Three electronic readers 322 are coupled to the control panel 302. The three readers 322 are mounted on the sling 300. One of readers 322 is configured to read the patient tag 204 and the caregiver tag 206. The other two readers are configured to read tags 150, 152, 154, 156 of the respective loops 120, 140 of sling 300 and to read tags attached to sling bar 44 near the hooks 166, 168 and to read a tag on the coupler 43 or the coupler 748, as the case may be, which indicates the type of patient lift system 12, 14 to which the sling 300 is attached. Thus, in the FIG. 12 embodiment, the sling 300 includes the electronic readers 322 and not the sling bar 44.

The control panel 302 includes a processor and memory that operate to implement the software logic to determine the proper attachment, or improper attachment, of sling 300 to sling bar 44 and that operate to confirm that a proper patient is supported by sling 300 and that a proper caregiver is operating the respective patient lift system 12, 14. Thus, the readers 322 send tag identification signals to control panel 302 to ensure that the sling 300 is properly attached to the sling bar 44 and that the patient and the caregiver are proper before the control panel 302 becomes operational to send signals to control system 54 or control unit 802 to operate the motor 64 or actuator 804 as the case may be. In some embodiments, the control panel 302 tracks a number of times that the various tags are detected to track a usage of the sling 300.

User inputs 330 are provided on the control panel 302 to operate the lift system 10. The user inputs 330 include an up button 332 and a down button 334 that may be used to raise and lower the sling 300, respectively, after control panel 302 becomes enabled or operational. In some embodiments, the user inputs 330 are only operational if sling 300 is in use. For example, if the switch 310 detects a patient on the sling 300, the control panel 302 enables the user inputs 330 in some embodiments. In other embodiments, the user inputs 330 are only enabled for use if switch 310 detects a patient and if the electronic readers read 322 the proper identification signals from the tags and send respective signals to the control panel 302 to enable the user inputs 330.

In some embodiments, the control panel 302 also includes an accelerometer 340. The accelerometer 340 is used to determine that the sling 300 is in use. For example, the accelerometer 340 may detect when weight is applied to the sling 300 and pulls the sling 300 downwardly. In some embodiments, the lift system 10 is only enabled if the accelerometer 340 detects that the sling 300 is in use.

In other embodiments, the accelerometer 340 is used to detect that the sling 300 is being laundered. During a laundry cycle, the sling 300 is moved at a high speed that is detected by the accelerometer 340. The control panel 302 monitors each time that the high speed is detected to track the number of times that the sling 300 has been laundered. The control panel 302 may also include a humidity sensor 342 that detects when the sling 300 is being laundered. In some embodiments, the control panel 302 only tracks a laundry cycle when both the accelerometer 340 and the humidity sensor 342 detect laundering. In other embodiments, only one of the accelerometer 340 or the humidity sensor 342 is used to detect laundering and for the control panel 302 to track a laundry cycle.

The control panel 302 also includes operational indicators 350. The operational indicators 350 include an on indicator 352 and an off indicator 354. For example, the on indicator 352 may be a green light that indicates that the lift system is operational. That is, when the sling 300 is detected on the sling bar 44 (as described above) and/or when a patient is detected on the sling 300 (as described above), the on indicator 352 is illuminated. The off indicator 354 may be illuminated if the lift system 10 is not operational due to the sling 300 being improperly coupled to the sling bar 44 and/or an improper patient being detected on the sling 300 and/or an unqualified caregiver attempting to operate the patient lift system 10.

Figure 13:
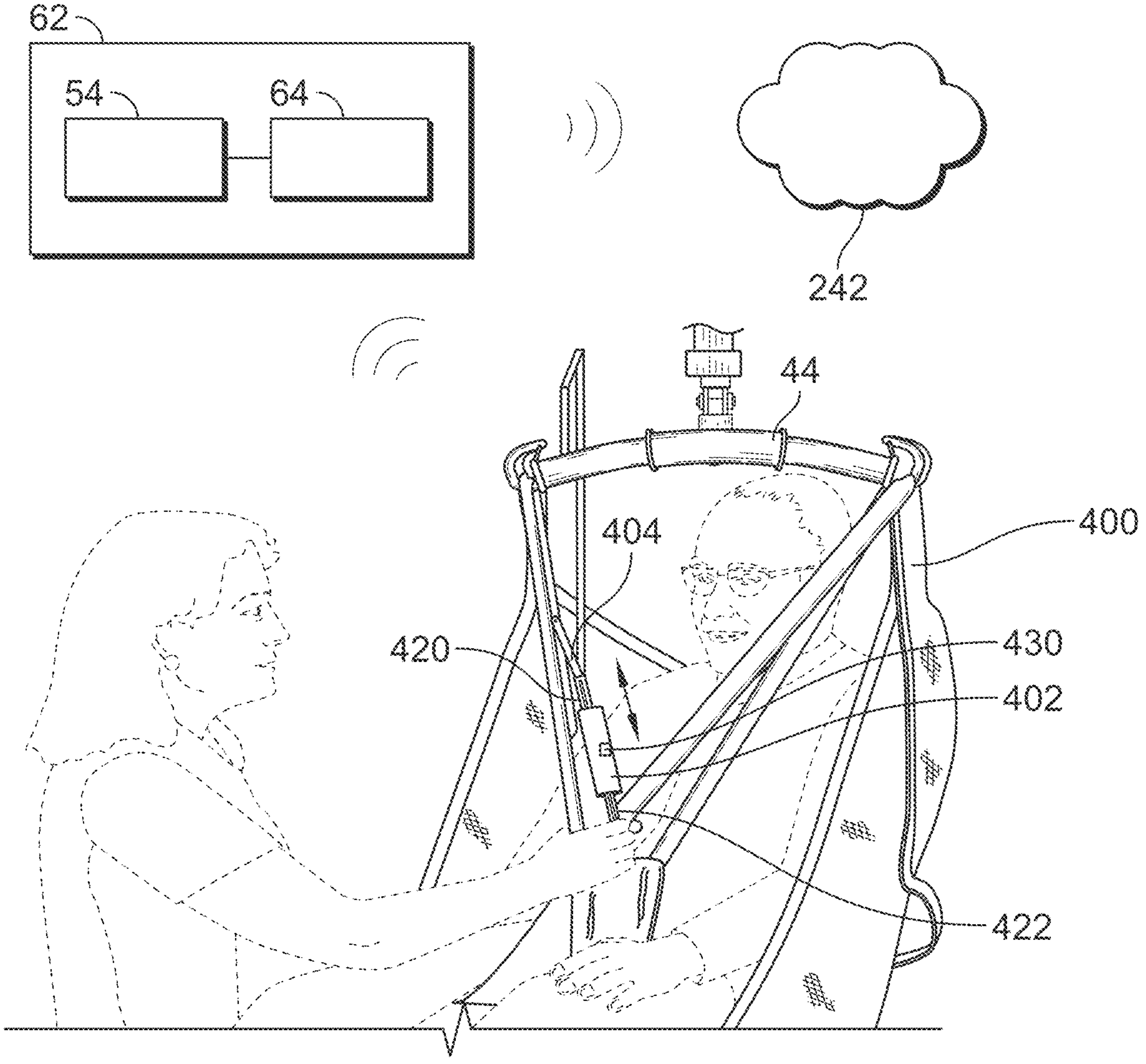
FIG. 13 is a front perspective view of a sling in accordance with an alternative embodiment of the present disclosure showing a handle to raise and lower the sling incorporated into one of the loops of the respective leg section of the sling.

Referring now to FIG. 13, a sling 400 includes a handle 402 for adjusting a height of the sling 400. In some embodiments, the sling 400 may include any of the features described above in connection with slings 50 and sling 300. The handle 402 is attached to a strap 404 of one of the leg sections of the sling 400 so that the handle is accessible to a caregiver. The handle 402 is in communication with the control system 54 of the sling bar 44. Movement of the handle 402 generates a signal to the control system 54 that includes instructions to operate the motor 64 of the lift system 10. For example, if the handle 402 is pulled downwardly, the motor 64 is operated to lower the sling bar 44. Likewise, if the handle 402 is pulled upwardly, the motor 64 is operated to raise the sling bar 44. In some embodiments, the handle 402 slides by a limited amount along the strap 420 in upward and downward directions to provide the signal to raise and lower sling bar 44.

In some embodiments, the handle 402 includes an upper strain gauge 420 that extends between the handle 402 and the strap 404. When the handle 402 is pulled downwardly, the upper strain gauge 420 detects tension and a signal is sent to the control system 54 to lower the sling bar 44. The handle 402 may also include a lower strain gauge 422 that extends between the handle 402 and the strap 404. When the handle 402 is pulled upwardly, the lower strain gauge 422 detects tension and a signal is sent to raise the sling bar 44.

In other embodiments, the handle 402 includes an accelerometer 430. The accelerometer 430 detects movement of the handle 402. When the accelerometer 430 detects that the handle 402 is being moved upwardly, a signal is sent to the control system 54 instructing the motor 64 to lift the sling bar 44. Likewise, when the accelerometer detects that the handle 402 is moved downwardly, a signal is sent to the control system 54 instructing the motor 64 to lower the sling bar 44.

It should be noted that the handle 402 may be used with any of the above described systems for preventing and allowing operation of the motor 64. For example, to prevent injury or accident, the handle 402 may only be operational to operate the motor 64 when the sling 400 is determined to be properly positioned on the sling bar 44, when the patient is identified as a proper patient, and/or when the caregiver is identified as a proper caregiver. In other embodiments, contact switches, string gauges, or Hall effect sensors are used in lieu of strain gauges 422 to detect the movement of handle 402 upwardly and downwardly.

Figure 14:
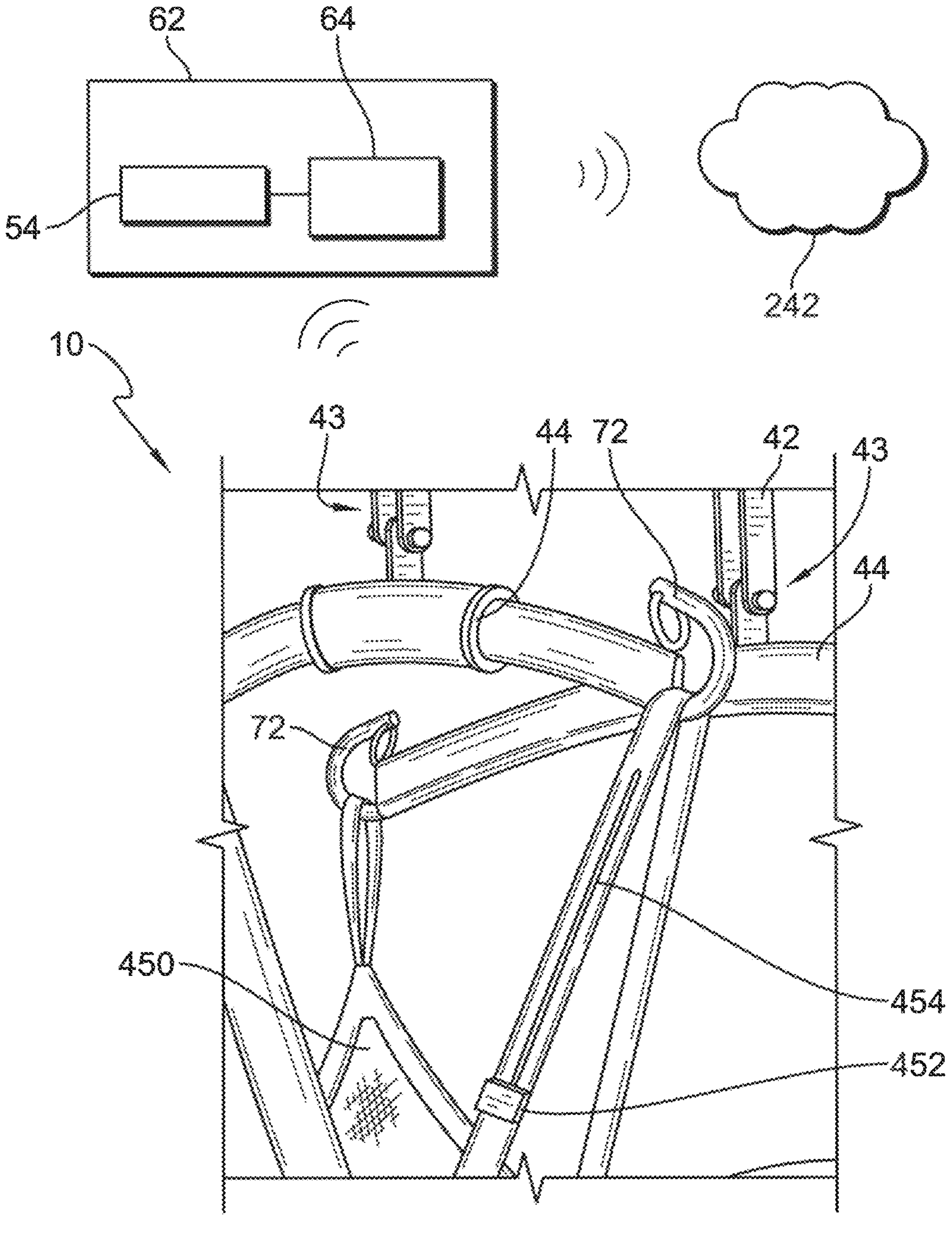
FIG. 14 is a front perspective view of a sling in accordance with another embodiment of the present disclosure used in a dual sling bar system having four hooks for coupling to individual loops of the sling and showing the sling having a strain gauge in the form of a thread-gauge woven into one of the loops of the sling to detect usage of the sling, the strain gauge being coupled to a wireless communication device for wireless communication with the controller of the lift housing unit that raises and lowers the dual sling bars in unison.

FIG. 14 illustrates a sling 450 that may have features that are the same as any of the above described embodiments of slings 50, 300, 400. The sling 450 includes a control panel 452 having a strain gauge 454. The strain gauge 454 is threaded into the fabric of a strap 456 of the sling 450. The strain gauge 454 is configured as a thread-gauge in the webbing of strap 456 to detect pulling on the strap 456. For example, when weight is applied to the sling 450 from a patient positioned in the sling 450, the strain gauge 454 detects tension in the strap 456.

The control panel 452 includes a wireless communication device, such as a transmitter or transceiver, to communicate signals when tension is detected in the strap 456. For example, the control panel 452 may send a signal to the control system 54 of the lift system 10 to enable the number of uses of the sling 450 to be tracked and to enable operation of the motor 64 unless the strain gauge 454 senses an overload condition on the sling 450 due to too much patient weight. The number of uses of the sling 450 is stored in control panel 452 in some embodiments and is incremented each time sling 450 is used. The control system 54 disables motor 64 if the number of uses transmitted from control panel 452 exceeds a threshold amount of uses.

In other embodiments, the control panel 452 communicates with a remote device 192 via network 242 for example. The remote device 192 may monitor each time that tension is detected in the strain gauge 454 to track the usage of the sling 450. In some embodiments, the strain gauge 454 is required to detect a predetermined weight prior to any signals being transmitted from the control panel 452. Accordingly, the usage of the sling 450 is only tracked when the predetermined weight is exceeded. Likewise, the motor 64 may be disabled if the patient weight exceeds an upper limit of patient weight for the sling 450.

In the illustrative embodiment of FIG. 14, a dual sling bar system 10 is shown. That is, the sling 450 is coupled to two sling bars 44. The two sling bars 44 have four hooks 72 for coupling to individual loops of the sling 450. The lift assemblies 22 associated with the two sling bars 44 are operated to raise and lower the dual sling bars 44 in unison. In some embodiments of the dual sling bar system 10, electronic readers 180, 182 are provided in each sling bar 44 and are used to detect the tags 150, 152, 154, 156 attached to each of the loops of the sling 450. The control system 54 is programmed so as to confirm that the proper loops of sling 450 are attached to the corresponding hooks of the two sling bars 44. Control system 54 disables motors 64 of the two lift assemblies 22 if the tags 150, 152, 154, 156 read by the electronic readers 180, 182 indicate that the loops of sling 450 are attached to hooks 72 of sling bars 44 in an improper manner. In some embodiments, a dual sling bar (not shown) has a strut or beam interconnecting the two sling bars 44 and then a single lift assembly 22 has its strap 42 connected to the strut or beam to raise and lower the dual sling bar. Such a dual sling bar may be used with patient lift system 14 of FIG. 2 if desired.

Figure 16:
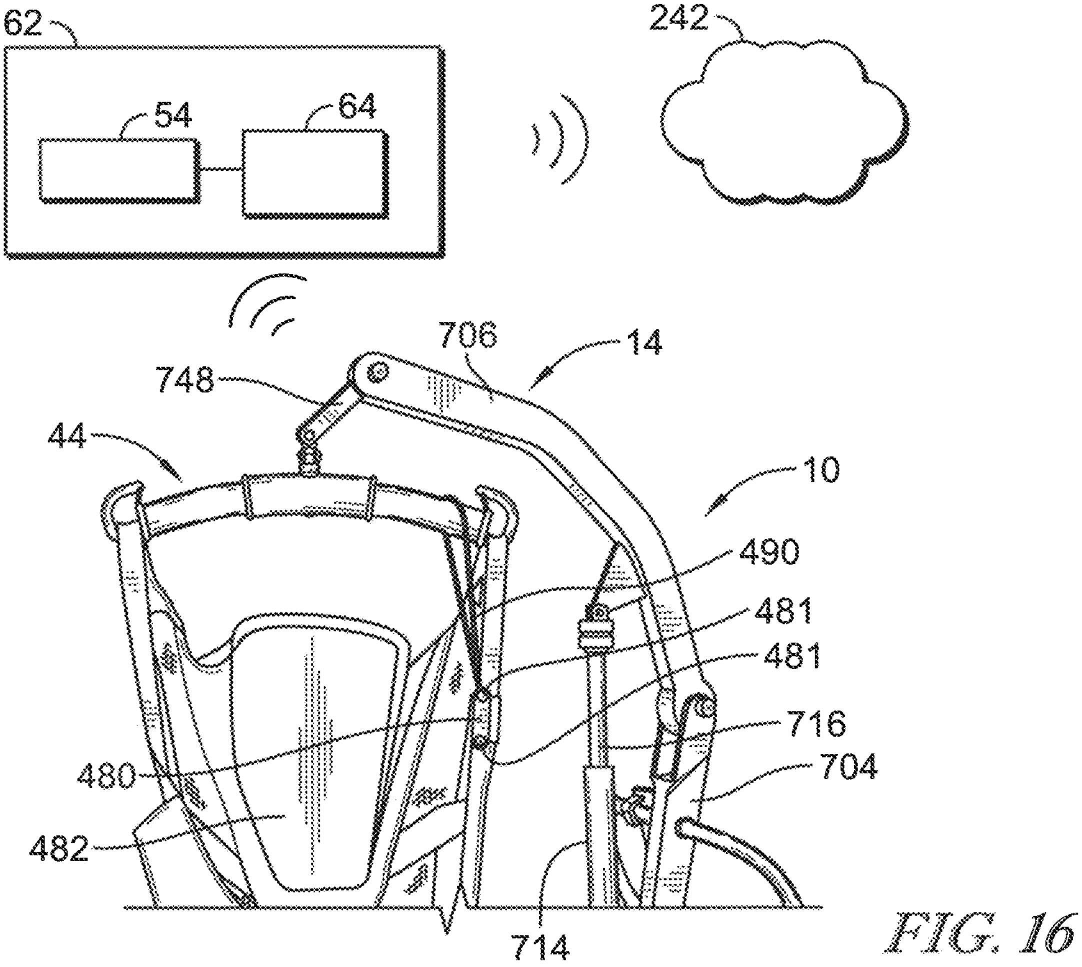
FIG. 16 is a front elevation view showing a retractable tether interconnecting the lift system controller of FIG. 15 with the sling bar of the mobile patient lift system of FIG.

Referring now to FIG. 15, a control unit 480 for the lift system 10 is illustrated on a sling 482. The control unit 480 may be used with any of the slings 50, 300, 400, 450 described above. The control unit 480 is removably coupled to the sling 482. In the illustrative embodiment, the control unit 480 is removably coupled to a strap 484 of the sling 482. In other embodiments, the control unit 480 may be removably coupled to other sections of the sling 482. As illustrated in FIG. 16, the control unit 480 is also coupled to the lift bar 160 with a tether 490 that is attached to one a pair of loops 481 molded into the control unit 480 at opposite ends thereof. In some embodiments, the tether 490 is a retractable tether that retains the control unit 480 at the sling bar 44 when the control unit 480 is detached from sling 482. When in use, the control switch 480 may be pulled downwardly from the sling bar 44 and attached to the sling 482 at an desired location along the peripheral edge of the sling 482 but typically, control unit 480 is attached to one of the straps, such as strap 484, of the sling 482.

The control unit 480 attaches to the sling 484 to free a hand of the caregiver operating the lift system 10. By attaching the control unit 480 to the strap 484 of the sling 482, the caregiver can use one hand to simultaneously guide the sling 482 and operate the control unit 480. Accordingly, the caregiver then has a free hand to hold the patient and maintain the patient's position on the sling 482 while the lift system 10 is operated.

An embodiment of control unit 480 is illustrated in FIGS. 17 and 18. As shown in FIG. 18, a back side 500 of the control unit 480 includes a clip 502 that is configured to clip onto the sling 482. In other embodiments, the control unit 480 may include other attachment mechanisms, i.e. hook and loop fasteners, buttons, snaps, or the like. The clip 502 allows the caregiver to quickly attach and remove the control unit 480 to and from the sling 482.

A front side 504 of the control unit 480 (illustrated in FIG. 17) includes user inputs 510. The user inputs 510 include a first button 512 and a second button 514. The first button 512 includes an arrow 520 that points in an opposite direction from an arrow 522 on the second button 514. The control unit 480 is configured to be positioned on the sling 482 in any orientation. That is, the first button 512 may be a top button, and the second button 514 may be a bottom button. When oriented in an opposite direction, the first button 512 may be a bottom button, and the second button 514 may be a top button.

The control unit 480 determines its orientation relative to the sling 482 to assign the functions of buttons 512, 514. That is, the button 512, 514 that is positioned with its arrow 520, 522 pointing upwardly is assigned as the top button. The button 512, 514 that is positioned with its arrow 520, 522 pointing downwardly is assigned as the bottom button. The control unit 480 communicates with the control system 54 of the lift system 10, either through a wireless connection or a wired connection, such as through the tether 490, to control the motor 64 of the lift system 10. When the button 512, 514 assigned as the top button is actuated, the motor 64 raises the sling bar 44. When the button 512, 514 assigned as the bottom button is actuated, the motor 64 lowers the sling bar 44.

As illustrated in FIG. 19, the control unit 480 also includes a graphical user interface (GUI) 540 in some embodiments. The GUI 540 is illustrated between the buttons 512, 514; but may be positioned at any location on the front side 504 of the control unit 480. The GUI 540 may display alerts 546 regarding the lift system 10. For example, an alert 546 may be issued if the sling bar 44 is reaching a maximum or minimum height. Another alert 548 may indicate that maintenance is required for the lift system 10. The GUI 540 includes a lift system button 542 that may be actuated to provide information regarding the lift system 10. For example, by actuating the lift system button 542, the GUI 540 may display a height of the sling bar 44, a speed of the sling bar 44, or the like. A maintenance button 544 is provided to troubleshoot issues that may be occurring with the lift system 10.

Referring to FIG. 20, the buttons 512 and 514 are electrically coupled to a processor 560 and a memory 562. The memory 562 stores instructions that are performed by the processor 560 to operate the control unit 480. An accelerometer 564 is electrically coupled to the processor 560. The accelerometer 564 senses an orientation of the control unit 480. Based on a signal from the accelerometer 564, the processor 560 assigns the buttons 512 and 514 as the appropriate top button and bottom button.

When the top button and bottom button are actuated, the processor 560 sends a signal through an antenna 570 to the control system 54. If the top button is actuated, the processor 560 sends a signal instructing the lift system 10 to raise the sling bar 44. If the bottom button is actuated, the processor 560 sends a signal instructing the lift system 10 to lower the sling bar 44. In some embodiments, if the accelerometer 564 detects that the control switch 480 is tilted or otherwise not aligned straight up and down, the processor 560 may cause an alert 546 to be displayed on the GUI 540 as shown in FIG. 19.

A sling 600 having a main body section 602, a back section 604 extending upwardly from the main body section 602, and a pair of leg sections 606 extending downwardly from the main body section 602 opposite the back section 604 is shown in FIG. 21. The leg sections 606 include pressure sensors 610, for example load cells or piezoelectric sensors. As shown in FIG. 22, the sensors 610 only extend along the patient's legs and do not extend into the main body section 602 of the sling 600. The sensors 610 are configured to detect a level of pressure and/or shear being applied to the patient's legs when the patient is seated in the sling 600. By detecting the pressure and/or shear on the patient, a comfort of the patient may be improved by adjusting a position of the patient in the sling 600.

In some embodiments, the pressure sensors 610 are coupled to a transmitter 612 to transmit a signal indicating the detected pressure level and/or shear level to the remote device 192 via control system 54 and network 252. Accordingly, a caregiver carrying the remote device 192 or next to the remote device 192 can be alerted of the detected pressure level and/or shear level. In some embodiments, an alarm may be activated if the pressure level or shear level is too high. The alarm is communicated to the nurse call computer 192 in some embodiments. Alternatively or additionally, the transmitter 612 transmits a signal indicating the detected pressure level and/or shear level to the control system 54 for display on the display 236 and/or to the control unit 480 for display on the GUI 540 or other user interface of the lift system 10 so that the caregiver operating the lift system 10 is notified of the pressure level.

It should be noted that the pressure sensors 610 may be included in any of the embodiments of slings 50, 300, 400, 450, 482, 600 described above. For example, operation of the motor 64 may be dependent on pressure being detected by the sensors 610. Accordingly, operation of motor 64 is disabled if either or both of pressure sensors 610 sense a pressure that exceeds a threshold amount in some embodiments. In some embodiments, pressure sensors 610 include capacitive sensors or force resistive sensors (FSR's) such as sensors made of resistive ink.

Although this disclosure refers to specific embodiments, it will be understood by those skilled in the art that various changes in form and detail may be made without departing from the subject matter set forth in the accompanying claims.

The invention claimed is:

1. A person lift system comprising:

a motor, a sling bar coupled to the motor, the sling bar including an attachment hook, a sling including a main body section and a loop coupled to the main body section, the loop configured to attach to the attachment hook, an electronic reader coupled to the sling bar near the attachment hook, a short range wireless tag coupled to the loop at a position spaced apart from the main body section, wherein the electronic reader reads short range tag identification signals from the short range wireless tag to determine whether the loop is coupled to the attachment hook, wherein the sling is configured so that the short range wireless tag is closer to the attachment hook than to the main body section when the loop is coupled to the attachment hook and an occupant is supported by the sling, and an accelerometer coupled to the loop and configured to determine an orientation of the loop with respect to a direction of gravity or with respect to horizontal.

2. The person lift system of claim 1, wherein the accelerometer determines movement of the sling so that a processor is able to determine whether the sling is in a laundry cycle.

3. The person lift system of claim 1, further comprising a control system to control the motor, wherein the control system is enabled in response to the electronic reader reading the short range wireless tag.

4. The person lift system of claim 3, wherein the control system tracks a number of person lift system uses based on the electronic reader reading the short range wireless tag.

5. The person lift system of claim 1, further comprising a user input configured to operate the motor.

6. The person lift system of claim 5, wherein the user input is coupled to the sling.

7. The person lift system of claim 5, wherein the user input is detachably coupled to the sling.

8. The person lift system of claim 1, wherein the short range wireless tag includes a radio frequency identification tag.

9. The person lift system of claim 1, wherein the attachment hook is moveable between and an open position and a closed position, and the attachment hook includes a sensor to determine whether the attachment hook is in the open position or closed position.

10. The person lift system of claim 9, wherein the electronic reader is powered in response to the sensor indicating that the attachment hook has been moved to the open position.

11. The person lift system of claim 1, further comprising a switch positioned in the sling and a spring coupled to the switch, wherein the spring enables the switch in response to weight being applied to the sling, and wherein, in response to the switch being activated, power is supplied to the short range wireless tag.

12. The person lift system of claim 1, further comprising a humidity sensor positioned in the sling to detect that the sling is being laundered.

13. The person lift system of claim 1, further comprising a wireless communication device positioned in the sling to communicate to a remote device that the sling is in use.

14. The person lift system of claim 13, wherein the remote device is operable to determine a location of the sling.

15. The person lift system of claim 1, wherein the sling further comprises a leg section coupled to the main body section, wherein the leg section includes at least one pressure sensor to detect a pressure on a patient in the sling.

16. The person lift system of claim 15, wherein the main body section does not include pressure sensors.

17. The person lift system of claim 1, further comprising a handheld controller having a clip configured to attach to the loop, the handheld controller having user inputs that are configured to control the motor.

18. The person lift system of claim 17, wherein the user inputs include a first button and a second button, wherein one of the first button and the second button is usable to actuate the motor to raise the sling bar and the other of the first button and the second button is usable to actuate the motor to lower the sling bar.

19. The person lift system of claim 17, wherein the handheld controller includes a second accelerometer to determine an orientation of the handheld controller, wherein a signal from the second accelerometer is used by a processor to determine an upper button of the first button and the second button and a lower button of the first button and the second button.

20. The person lift system of claim 19, wherein the upper button is configured to actuate the motor to raise the sling bar, and wherein the lower button is configured to actuate the motor to lower the sling bar.

21. The person lift system of claim 17, further comprising a retractable cord coupling the handheld controller to the sling bar.

22. A person lift system comprising:

a motor, a sling bar coupled to the motor, the sling bar including an attachment hook, a sling including a main body section and a loop coupled to the main body section, the loop configured to attach to the attachment hook, an electronic reader coupled to the sling bar near the attachment hook, a short range wireless tag coupled to the loop, wherein the electronic reader reads short range tag identification signals from the short range wireless tag to determine whether the loop is coupled to the attachment hook, an accelerometer coupled to the loop and configured to determine an orientation of the loop with respect to a direction of gravity or with respect to horizontal, a user input configured to operate the motor, and a retractable tether coupling the user input to the sling bar.

* * * * *